(12) United States Patent
Wang et al.

(10) Patent No.: US 11,926,810 B2
(45) Date of Patent: Mar. 12, 2024

(54) BIOREACTOR WITH SCAFFOLDS

(71) Applicant: 3D BIOTEK, LLC, Warren, NJ (US)

(72) Inventors: Zongsen Wang, Princeton, NJ (US); Wing Lau, Basking Ridge, NJ (US); Faribourz Payvandi, Belle Mead, NJ (US); Peng Yue, Vista, CA (US); Azadeh Jadali, Coram, NY (US); Peter Materna, Metuchen, NJ (US)

(73) Assignee: 3D Biotek, LLC, Warren, NJ (US)

( * ) Notice: Subject to any disclaimer, the term of this patent is extended or adjusted under 35 U.S.C. 154(b) by 0 days.

(21) Appl. No.: 18/076,203

(22) Filed: Dec. 6, 2022

(65) Prior Publication Data
US 2023/0112777 A1 Apr. 13, 2023

Related U.S. Application Data

(63) Continuation of application No. 16/863,220, filed on Apr. 30, 2020, now Pat. No. 11,566,215, which is a
(Continued)

(51) Int. Cl.
*C12M 1/00* (2006.01)
*C12M 1/02* (2006.01)
(Continued)

(52) U.S. Cl.
CPC .......... *C12M 23/34* (2013.01); *C12M 21/08* (2013.01); *C12M 23/40* (2013.01); *C12M 25/02* (2013.01);
(Continued)

(58) Field of Classification Search
CPC ...... C12M 23/34; C12M 23/40; C12M 23/04; C12M 21/08; C12M 25/02; C12M 25/14; C12M 27/00; C12M 27/02; C12M 29/10
See application file for complete search history.

(56) References Cited

U.S. PATENT DOCUMENTS

| 4,138,463 A | 2/1979 | Moneghan |
| 4,693,983 A | 9/1987 | Davies et al. |

(Continued)

FOREIGN PATENT DOCUMENTS

| CN | 2099763 U | 3/1992 |
| CN | 101402917 B | 4/2009 |

(Continued)

OTHER PUBLICATIONS

NIST, "Tissue Engineering Reference Scaffolds for Cell Culture", Report of Investigation Reference Material 8394, Apr. 2013, pp. 1-7.
(Continued)

*Primary Examiner* — Michael L Hobbs
(74) *Attorney, Agent, or Firm* — Corner Counsel, LLC

(57) ABSTRACT

A bioreactor includes a reservoir container for holding a liquid medium, a duct providing a flowpath in a generally vertical direction upward from the reservoir container, a plurality of fiber assemblies located within the duct, a top of which is higher than a top of the plurality of fiber assemblies, and a circulation system. The upper end of the duct comprises an overflow wall surrounded by a moat, a bottom of which is lower than a top of the overflow wall. The upper end of the duct and moat contact a pocket region that is bounded by a structure that is connected to the duct and that is isolated from fluid communication with an exterior of the pocket region. The liquid medium flows over the overflow wall within the pocket region, contacts gas in the pocket region, overflows into the moat and is removed therefrom by the circulation system.

16 Claims, 25 Drawing Sheets

Related U.S. Application Data continuation of application No. 15/686,211, filed on Aug. 25, 2017, now abandoned.

(60) Provisional application No. 62/380,414, filed on Aug. 27, 2016.

(51) Int. Cl.
  *C12M 1/06* (2006.01)
  *C12M 1/12* (2006.01)
  *C12M 3/00* (2006.01)

(52) U.S. Cl.
  CPC ............ *C12M 25/14* (2013.01); *C12M 27/00* (2013.01); *C12M 27/02* (2013.01); *C12M 29/10* (2013.01)

(56) References Cited

U.S. PATENT DOCUMENTS

| | | |
|---|---|---|
| 4,988,623 A | 1/1991 | Schwarz et al. |
| 5,026,650 A | 6/1991 | Schwarz et al. |
| 5,081,035 A | 1/1992 | Halberstadt et al. |
| 5,151,368 A | 9/1992 | Brimhall et al. |
| 5,190,878 A | 3/1993 | Wilhelm |
| 5,202,254 A | 4/1993 | Amiot et al. |
| 5,266,480 A | 11/1993 | Naughton |
| 5,342,781 A | 8/1994 | Su |
| 5,416,022 A * | 5/1995 | Amiot .................... C12M 25/02 435/297.2 |
| 5,501,971 A | 3/1996 | Freedman et al. |
| 5,510,254 A | 4/1996 | Naughton et al. |
| 5,565,361 A | 10/1996 | Mutsakis et al. |
| 5,591,627 A | 1/1997 | Miyamoto |
| 5,612,188 A | 3/1997 | Shuler et al. |
| 5,646,043 A | 7/1997 | Emerson et al. |
| 5,764,521 A | 6/1998 | Batchelder |
| 5,766,949 A | 6/1998 | Liau et al. |
| 5,770,417 A | 6/1998 | Vicanti et al. |
| 5,843,766 A | 12/1998 | Applegate et al. |
| 5,858,721 A | 1/1999 | Naughton et al. |
| 5,928,945 A | 7/1999 | Seliktar et al. |
| 5,979,794 A | 11/1999 | DeFillipi et al. |
| 5,989,913 A | 11/1999 | Anderson et al. |
| 6,001,643 A | 12/1999 | Spaulding |
| 6,121,042 A | 9/2000 | Peterson et al. |
| 6,140,039 A | 10/2000 | Naughton et al. |
| 6,143,293 A | 11/2000 | Weiss et al. |
| 6,218,182 B1 | 4/2001 | Naughton et al. |
| 6,323,022 B1 | 11/2001 | Chang et al. |
| 6,592,751 B2 | 7/2003 | Haridas |
| 6,673,595 B2 | 1/2004 | Barbera-Guillem |
| 6,730,252 B1 | 5/2004 | Teoh |
| 6,841,384 B2 | 1/2005 | Robbins, Jr. |
| 6,844,187 B1 | 1/2005 | Wechsler et al. |
| 6,875,605 B1 | 4/2005 | Ma |
| 6,911,201 B1 | 6/2005 | Merchav et al. |
| 6,995,013 B2 | 2/2006 | Connelly et al. |
| 7,033,823 B2 | 4/2006 | Chang |
| 7,041,493 B2 | 5/2006 | Rao |
| 7,048,963 B2 | 5/2006 | Braithwaite et al. |
| 7,112,441 B2 | 9/2006 | Uemura et al. |
| 7,122,371 B1 | 10/2006 | Ma |
| 7,163,825 B2 | 1/2007 | Gault |
| 7,174,282 B2 | 2/2007 | Hollister et al. |
| 7,198,940 B2 | 4/2007 | Vellinger et al. |
| 7,198,941 B2 | 4/2007 | Fadnavis et al. |
| 7,270,996 B2 | 9/2007 | Cannon et al. |
| 7,291,500 B2 | 11/2007 | Uemura et al. |
| 7,348,175 B2 | 3/2008 | Vilendrer et al. |
| 7,348,176 B2 | 3/2008 | DiMilla et al. |
| 7,371,400 B2 | 5/2008 | Borenstein et al. |
| 7,410,792 B2 | 8/2008 | Vilendrer |
| 7,416,884 B2 | 8/2008 | Gemmiti et al. |
| 7,527,965 B2 | 5/2009 | Ozil |
| 7,537,693 B2 | 5/2009 | Zhao et al. |
| 7,604,987 B2 | 10/2009 | Hutmacher et al. |
| 7,745,209 B2 | 6/2010 | Martin et al. |
| 7,749,749 B2 | 7/2010 | Ting et al. |
| 7,754,478 B2 | 7/2010 | Suzuki et al. |
| 7,767,446 B2 | 8/2010 | Robbins et al. |
| 7,855,070 B2 | 11/2010 | Vukasinovic et al. |
| 7,892,821 B2 | 2/2011 | Watanabe et al. |
| 7,906,323 B2 | 3/2011 | Cannon et al. |
| 7,919,307 B2 | 4/2011 | Klaus et al. |
| 7,968,026 B1 | 6/2011 | Teoh et al. |
| 8,071,007 B1 | 12/2011 | Teoh et al. |
| 8,105,380 B2 | 1/2012 | Kharazi et al. |
| 8,321,145 B2 | 1/2012 | Antwiler |
| 8,110,213 B2 | 2/2012 | Mikos et al. |
| 8,128,924 B2 | 3/2012 | Naughton et al. |
| 8,163,555 B2 | 4/2012 | Antwiler |
| 8,173,420 B2 | 5/2012 | Moreno et al. |
| 8,216,831 B2 | 7/2012 | Kobayashi et al. |
| 8,260,063 B2 | 9/2012 | Hasezawa et al. |
| 8,273,572 B2 | 9/2012 | Martin et al. |
| 8,278,101 B2 | 10/2012 | Navran, Jr. |
| 8,309,347 B2 | 11/2012 | Antwiler |
| 8,318,479 B2 | 11/2012 | Domansky et al. |
| 8,383,395 B2 | 2/2013 | Hata et al. |
| 8,383,397 B2 | 2/2013 | Wojciechowski et al. |
| 8,399,245 B2 | 3/2013 | Leuthaeuser et al. |
| 8,415,157 B2 | 4/2013 | Tazaki et al. |
| 8,415,159 B2 | 4/2013 | Ward et al. |
| 8,431,401 B2 | 4/2013 | Watanabe et al. |
| 8,435,782 B2 | 5/2013 | Nishi et al. |
| 8,445,266 B2 | 5/2013 | Kiyota et al. |
| 8,463,418 B2 | 6/2013 | Liu et al. |
| 8,481,305 B2 | 7/2013 | Kim et al. |
| 8,492,135 B2 | 7/2013 | Porter et al. |
| 8,492,140 B2 | 7/2013 | Smith et al. |
| 8,401,460 B2 | 8/2013 | Furey |
| 8,506,162 B2 | 8/2013 | Schick et al. |
| 8,507,263 B2 | 8/2013 | Asnaghi et al. |
| 8,513,003 B2 | 8/2013 | Moreno et al. |
| 8,540,499 B2 | 9/2013 | Page et al. |
| 8,546,142 B2 | 10/2013 | Martin et al. |
| 8,569,050 B1 | 10/2013 | Ericsson |
| 8,617,879 B2 | 12/2013 | Yu et al. |
| 8,673,640 B2 | 3/2014 | Chen et al. |
| 8,702,808 B2 | 4/2014 | Teoh et al. |
| 8,735,117 B2 | 5/2014 | Darling et al. |
| 8,741,631 B2 | 6/2014 | Le et al. |
| 8,785,180 B2 | 7/2014 | Zhang et al. |
| 8,785,181 B2 | 7/2014 | Antwiler |
| 8,809,043 B2 | 8/2014 | Leuthaeuser et al. |
| 8,815,276 B2 | 8/2014 | Nygaard et al. |
| 8,815,585 B2 | 8/2014 | Beardsley et al. |
| 8,822,208 B2 | 9/2014 | Chokshi |
| 8,846,399 B2 | 9/2014 | Martin et al. |
| 8,852,933 B2 | 10/2014 | Porter et al. |
| 8,859,263 B2 | 10/2014 | Greenberger et al. |
| 8,864,844 B2 | 10/2014 | Ratcliffe et al. |
| 8,865,427 B2 | 10/2014 | Poo et al. |
| 8,865,460 B2 | 10/2014 | Orr et al. |
| 8,906,685 B2 | 12/2014 | Takayama et al. |
| 8,951,784 B2 | 2/2015 | Gould et al. |
| 8,986,979 B2 | 3/2015 | Castillo et al. |
| 9,005,918 B2 | 4/2015 | Dvorak et al. |
| 9,018,008 B2 | 4/2015 | Cho et al. |
| 9,057,044 B2 | 6/2015 | Israelowitz et al. |
| 9,057,045 B2 | 6/2015 | Gibbons et al. |
| 9,057,047 B2 | 6/2015 | Conte et al. |
| 9,057,715 B2 | 6/2015 | Kim et al. |
| 9,090,863 B2 | 7/2015 | Breuer et al. |
| 9,109,193 B2 | 8/2015 | Galliher et al. |
| 9,144,583 B2 | 9/2015 | Ariff et al. |
| 9,163,265 B2 | 10/2015 | Benson et al. |
| 9,175,259 B2 | 11/2015 | Nankervis |
| 9,206,383 B2 | 12/2015 | Vunjak-Novakovic et al. |
| 9,206,391 B2 | 12/2015 | Hase |
| 9,217,129 B2 | 12/2015 | Moretti et al. |
| 9,220,731 B2 | 12/2015 | Berry et al. |
| 9,220,732 B2 | 12/2015 | Curcio |
| 9,228,166 B2 | 1/2016 | Barrett et al. |

(56) References Cited

U.S. PATENT DOCUMENTS

| | | | |
|---|---|---|---|
| 9,228,579 B2 | 1/2016 | Stobbe |
| 9,249,383 B2 | 2/2016 | Yu et al. |
| 9,260,698 B2 | 2/2016 | Antwiler |
| 9,284,523 B2 | 3/2016 | Dodd et al. |
| 9,290,730 B2 | 3/2016 | Martin et al. |
| 9,309,491 B2 | 4/2016 | Martin et al. |
| 9,334,473 B2 | 5/2016 | Vukasinovic |
| 9,402,944 B2 | 8/2016 | Selden et al. |
| 9,405,300 B2 | 8/2016 | West |
| 9,506,867 B2 | 11/2016 | Moretto et al. |
| 9,512,393 B2 | 12/2016 | Kasuto et al. |
| 9,536,122 B2 | 1/2017 | Potyrailo |
| 9,567,560 B2 | 2/2017 | Honda et al. |
| 9,597,355 B2 | 3/2017 | Magnant |
| 9,617,506 B2 | 4/2017 | Jones et al. |
| 9,677,038 B2 | 6/2017 | Stobbe |
| 9,701,932 B2 | 7/2017 | Smith et al. |
| 10,426,884 B2 | 10/2019 | Labib et al. |
| 11,028,356 B2 | 6/2021 | Yuan et al. |
| 2002/0110905 A1 | 8/2002 | Barbera-Guillem |
| 2002/0113331 A1 | 8/2002 | Zhang |
| 2003/0054544 A1 | 3/2003 | Gruenberg |
| 2004/0029264 A1 | 2/2004 | Robbins, Jr. |
| 2004/0126405 A1 | 7/2004 | Sahatjian et al. |
| 2004/0132175 A1 | 7/2004 | Vetillard et al. |
| 2004/0241835 A1 | 12/2004 | Hutmacher et al. |
| 2004/0253716 A1 | 12/2004 | Jaeger et al. |
| 2005/0118711 A1 | 6/2005 | Nordheim et al. |
| 2005/0266393 A1 | 12/2005 | Baxter et al. |
| 2005/0276791 A1 | 12/2005 | Hansford et al. |
| 2005/0282268 A1 | 12/2005 | Kagayama |
| 2005/0287670 A1 | 12/2005 | Gulliver et al. |
| 2006/0094112 A1 | 5/2006 | Babalola et al. |
| 2006/0110822 A1* | 5/2006 | Robbins ............... C12M 29/10 435/293.1 |
| 2006/0195179 A1 | 8/2006 | Sun et al. |
| 2006/0211080 A1 | 9/2006 | Frost, III et al. |
| 2007/0026516 A1 | 2/2007 | Martin et al. |
| 2007/0128087 A1 | 6/2007 | Cannizzaro et al. |
| 2007/0148762 A1 | 6/2007 | Miyake et al. |
| 2007/0155273 A1 | 7/2007 | Chu et al. |
| 2008/0017558 A1 | 1/2008 | Pollock et al. |
| 2008/0076170 A1 | 3/2008 | Annala et al. |
| 2008/0085292 A1 | 4/2008 | Rezania et al. |
| 2008/0118974 A1 | 5/2008 | Martin et al. |
| 2008/0206734 A1 | 8/2008 | Asgari |
| 2008/0210623 A1 | 9/2008 | McMahon et al. |
| 2008/0213894 A1 | 9/2008 | Antwiler |
| 2008/0227190 A1 | 9/2008 | Antwiler |
| 2008/0248572 A1 | 10/2008 | Antwiler |
| 2008/0283469 A1 | 11/2008 | Pollock |
| 2008/0311650 A1 | 12/2008 | Jakob et al. |
| 2009/0104594 A1 | 4/2009 | Webb |
| 2009/0111180 A1 | 4/2009 | Vilendrer et al. |
| 2009/0215177 A1 | 8/2009 | Fryer et al. |
| 2009/0233361 A1 | 9/2009 | Farhat et al. |
| 2009/0238853 A1 | 9/2009 | Liu et al. |
| 2009/0312851 A1 | 12/2009 | Mishra |
| 2010/0190246 A1 | 7/2010 | Hase |
| 2010/0203624 A1 | 8/2010 | Singh |
| 2010/0233130 A1 | 9/2010 | Meretzki |
| 2011/0020923 A1 | 1/2011 | Lacey et al. |
| 2011/0091926 A1 | 4/2011 | Frerich |
| 2011/0124078 A1 | 5/2011 | Edwards et al. |
| 2011/0207209 A1 | 8/2011 | Hammons et al. |
| 2011/0229970 A1 | 9/2011 | Ma |
| 2011/0236970 A1 | 9/2011 | Larson et al. |
| 2011/0269226 A1 | 11/2011 | Van Noort et al. |
| 2011/0287508 A1 | 11/2011 | Chaudhuri et al. |
| 2012/0258440 A1 | 10/2012 | Jung et al. |
| 2012/0295248 A1 | 11/2012 | Cheng |
| 2012/0295338 A1 | 11/2012 | Reep et al. |
| 2013/0115588 A1 | 5/2013 | Davis et al. |
| 2013/0157353 A1 | 6/2013 | Dijkhuizen Borgart et al. |
| 2013/0177972 A1 | 7/2013 | Green et al. |
| 2013/0189723 A1 | 7/2013 | Felder et al. |
| 2013/0215252 A1 | 8/2013 | Pribenszky et al. |
| 2013/0260445 A1 | 10/2013 | Oura et al. |
| 2014/0030762 A1 | 1/2014 | Deplano et al. |
| 2014/0030805 A1 | 1/2014 | Kasuto et al. |
| 2014/0080212 A1 | 3/2014 | Asgari |
| 2014/0097137 A1 | 4/2014 | Ren et al. |
| 2014/0199679 A1 | 7/2014 | Panoskaltsis et al. |
| 2014/0255994 A1 | 9/2014 | Konstantinov et al. |
| 2014/0271571 A1 | 9/2014 | Magnant |
| 2014/0277461 A1 | 9/2014 | Nebosky et al. |
| 2014/0342447 A1 | 11/2014 | Aviles et al. |
| 2015/0017711 A1 | 1/2015 | Bennett et al. |
| 2015/0017715 A1 | 1/2015 | McDonald |
| 2015/0018968 A1 | 1/2015 | Sun et al. |
| 2015/0030514 A1 | 1/2015 | Feltham |
| 2015/0056703 A1 | 2/2015 | Johnson |
| 2015/0064780 A1 | 3/2015 | Hopkins et al. |
| 2015/0065588 A1 | 3/2015 | Weinberger et al. |
| 2015/0079584 A1 | 3/2015 | Gevaert et al. |
| 2015/0322399 A1 | 11/2015 | Purushothaman et al. |
| 2015/0367303 A1 | 12/2015 | Simon Soria |
| 2016/0024453 A1 | 1/2016 | Faustino Canadas et al. |
| 2016/0168528 A1 | 6/2016 | Roostoot et al. |
| 2016/0177244 A1 | 7/2016 | Conway et al. |
| 2016/0194591 A1 | 7/2016 | Castan et al. |
| 2016/0289633 A1 | 10/2016 | Yang et al. |
| 2017/0073625 A1 | 3/2017 | Kasuto et al. |
| 2017/0101618 A1 | 4/2017 | Kamen et al. |

FOREIGN PATENT DOCUMENTS

| | | | |
|---|---|---|---|
| CN | 100497582 C | 6/2009 |
| CN | 102057033 A | 5/2011 |
| CN | 102618442 A | 8/2012 |
| CN | 102296029 B | 1/2013 |
| CN | 203855588 U | 10/2014 |
| CN | 103966095 B | 1/2016 |
| CN | 105524832 A | 4/2016 |
| EP | 2130905 A1 | 12/2009 |
| EP | 2151491 | 10/2010 |
| EP | 2883685 A1 | 6/2015 |
| EP | 2913389 A1 | 9/2015 |
| NO | 2015061907 | 5/2015 |
| WO | 9504813 A1 | 2/1995 |
| WO | 03085080 A1 | 10/2003 |
| WO | 2009139703 A1 | 11/2009 |
| WO | 2010064943 A1 | 6/2010 |
| WO | 2012140519 A1 | 10/2012 |
| WO | 2014102730 | 7/2014 |
| WO | 2015052346 A1 | 4/2015 |
| WO | 2015095809 A1 | 6/2015 |
| WO | 2015158928 A1 | 10/2015 |
| WO | 2015165700 A1 | 11/2015 |
| WO | 2015176653 A1 | 11/2015 |
| WO | 2016036764 A1 | 3/2016 |
| WO | 2016050893 A1 | 4/2016 |
| WO | 2016069892 A1 | 5/2016 |

OTHER PUBLICATIONS

Amber Dance, "Cell culture goes 3-D with Devices that Better Mimic in Vivo Conditions", Enter the Third Dimension, Sep. 2022, pp. 1-8, The Scientist Magazine.

Zhao et al. Perfusion Bioreactor System for Human Mesenchymal Stem Cell Tissue Engineering: Dynamic Cell Seeding and Construct Development, Biotechnology Bioengineering, May 13, 2005 (132. 05.2005), vol. 91, Iss. 4, pp. 182-493.

Zahir, N, et al., "Death in the Third Dimension: Apoptosis Regulation and Tissue Architecture," Current opinion in Genetics and Development, vol. 14, 2004, p. 71-80.

Dhiman, et al., "Characterization and Evaluation of Chitosan Matrix for In Vitro Growth of MCF-7 Breast Cancer Cell Lines," Biomaterials, vol. 25, 2004, p. 5147-5154.

Abbot, A., et al., "Cell Culture: Biology's New Dimension," Nature, vol. 424, Aug. 2003, p. 870-872.

(56) References Cited

OTHER PUBLICATIONS

Baker, S., et al., "Characterization of Electrospun Polystyrene Scaffolds for Three-Dimensional In Vitro Biological Studies," Biomaterials, vol. 27, 2006, p. 3136-3146.
Schmeichel, K., et al. "Modeling Tissue-Specific Signaling and Organ Function in Three Dimensions," Journal of Cell Science, vol. 116, 2003, 2377-2388.
Hutmacher, D., et al., "Scaffold Design and Fabrication Technologies for Engineering Tissues—State of the Art and Future Perspectives," Journal of Biomaterials Science, Polymer Edition, vol. 12, No. 1, 2001, p. 107-124.
Hayman, M.W., et al. "Growth of Human Stem Cell-Derived Neurons on Solid Three-Dimensional Polymers," Journal of Biochemical and Biophysical Methods, vol. 62, 2005, p. 231-240.
Ferrera, D., et al., "Three-Dimensional Cultures of Normal Human Osteoblasts: Proliferation and Differentiation Potential In Vitro and Upon Ectopic Implantation in Nude Mice," Bone, vol. 30, No. 5, May 2002, p. 718-725.
Kale, S., et al., "Three-Dimensional Cellular Development is Essential for Ex Vivo Formation of Human Bone," Nature Biotechnology, vol. 18, Sep. 2000, p. 954-958.
Martin, I., et al., "The Role of Bioreactors in Tissue Engineering," Trends in Biotechnology, vol. 22, No. 2, Feb. 2004. p. 80-86.
Tallheden, T., et al., "Gene Expression During Redifferentiation of Human Articular Chondrocytes," OsteoArthritis and Cartilage, vol. 12, 2004, p. 525-535.
International Preliminary Report on Patentability received in PCT/US2008/073433, dated Nov. 19, 2008, 5 pages.
PCT Search Report and Written Opinion for PCT/US17/48523 dated Dec. 22, 2017.
Caicedo-Carvajal, Carlos E. et al., Cancer Tissue Engineering: A Novel 3D Polystyrene Scaffold for In vitro Isolation and Amplification. , Journal of Tissue Engineering, Aug. 2011.
Bergenstock et al., Polystyrene scaffolds: A novel tool for in vitro three-dimensional cancer models; First AACR Int'l Conf on Frontiers in Basic Cancer Research, Oct. 8-11, 2009.
Kumar et al. Human Mesenchymal Stem Cells Expansion on Three-Dimensional (3D) Printed Poly-Styrene (PS) Scaffolds . . . Procedia CIRP 65 (2017) 115-120.
Large Scale Cell Expansion 3D Biotek White Paper 2017.
Pall Life Sciences Xpansion® Multiplate Bioreactor System (brochure), 2015.
Pall Life Sciences XRS 20 Bioreactor System Rocker (brochure), 2013.
Pall Life Sciences iCELLis® Bioreactor Single-Use Bioreactor (brochure), 2015.
Larson, Brad; 3D Cell Culture White Paper Nov. 11, 2015.
Li, Luanfeng et al.; A Single-Use, Scalable Perfusion Bioreactor System, BioProcess International, pp. 46-54, Jun. 2009.

* cited by examiner

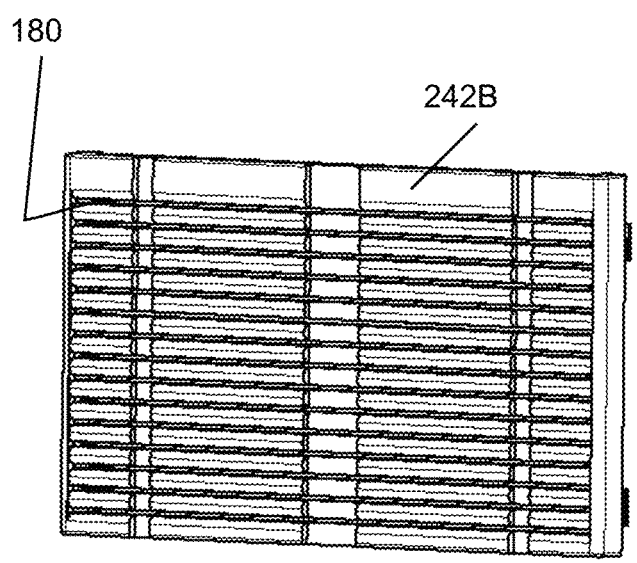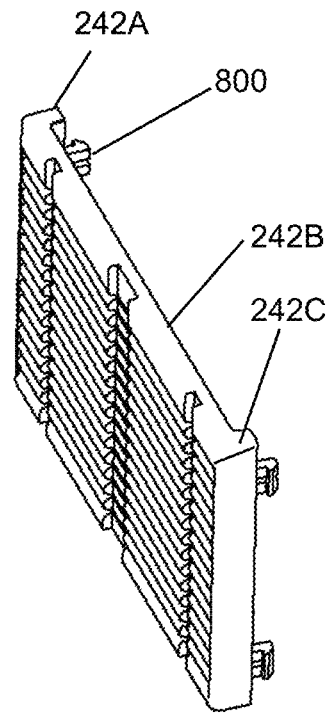
Figure 4A       Figure 4B
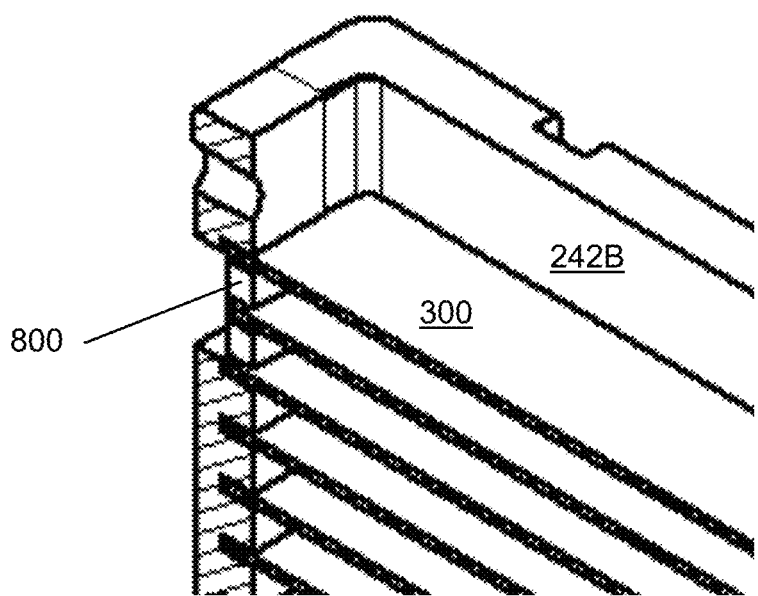
Figure 4C

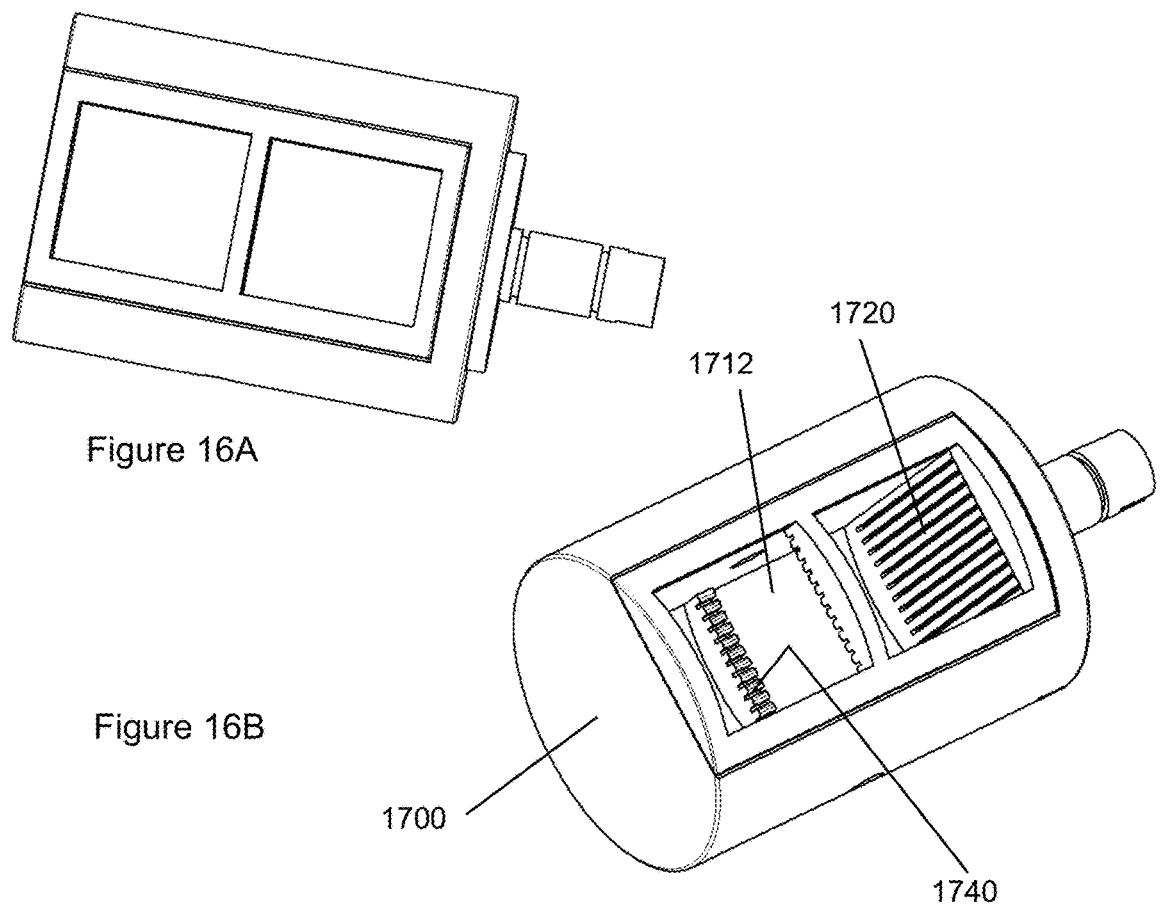
Figure 16A
Figure 16B
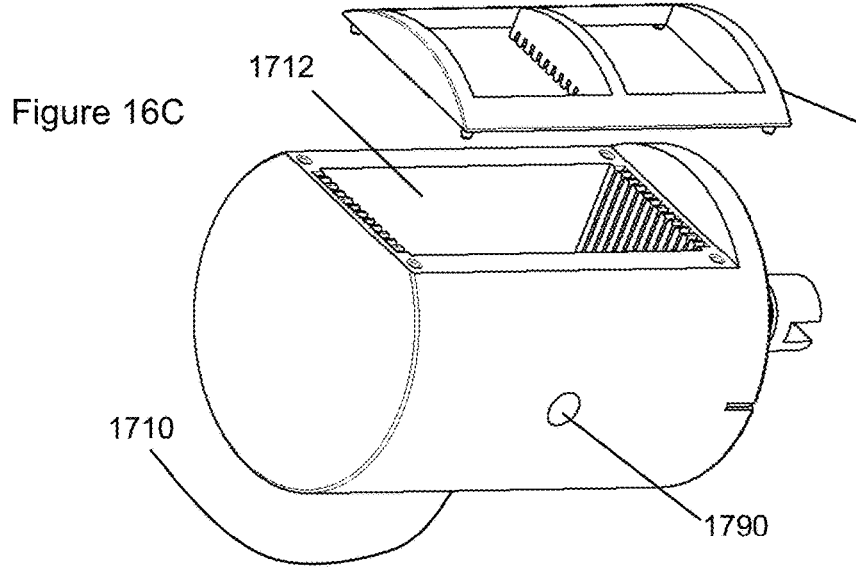
Figure 16C

BIOREACTOR WITH SCAFFOLDS

RELATED APPLICATIONS

This application is a continuation of U.S. patent application Ser. No. 16/863,220, filed Apr. 30, 2020, which is a continuation of U.S. patent application Ser. No. 15/686,211, filed Aug. 25, 2017, and claims the benefit of U.S. Provisional Patent Application No. 62/380,414, filed Aug. 27, 2016. The disclosures of all the aforementioned applications are incorporated herein by reference in their entireties.

FIELD OF THE INVENTION

Embodiments of the invention pertain to bioreactors.

BACKGROUND OF THE INVENTION

Bioreactors are used to expand a population of cells, such as stem cells or other anchorage dependent cells. However, improvements are still desirable, such as in regard to ease of use, and automation, and reproducibility of procedures. It is also desirable to culture so as to produce large numbers of cells, such as billions of cells if possible.

SUMMARY OF THE INVENTION

According to one embodiment of the invention, a bioreactor includes a reservoir container for holding a liquid medium; a duct providing a flowpath in a generally vertical direction upward from the reservoir container from a lower end of said duct to an upper end of said duct; a plurality of fiber assemblies located within the duct, a top of the duct being at a higher elevation than a top of the plurality of fiber assemblies; and a circulation system for causing the liquid medium to flow upwardly through the duct past or through the plurality of fiber assemblies. The upper end of the duct comprises an overflow wall surrounded on its outside by a moat, a bottom of the moat being at a lower elevation than the top of the overflow wall, the upper end of the duct and the moat being in contact with a pocket region, the pocket region being bounded by a structure that is connected to the duct, the pocket region being isolated from fluid communication with an exterior of the pocket region. When the circulation system is operating, the liquid medium flows over the overflow wall within the pocket region and the liquid medium is in contact with gas that is contained in the pocket region, and the liquid medium overflows into the moat and is removed from the moat by the circulation system.

According to another embodiment of the invention, a bioreactor includes a reservoir container for holding a liquid medium; a manifold assembly, the manifold assembly comprising an upper manifold and a lower manifold, the lower manifold having a lower end extending into the reservoir container; a holder holding a plurality of fiber assemblies that are suitable as scaffolds for cells; the d holder being able to be contained within the manifold assembly; and a circulating system for causing the liquid medium to flow through the manifold assembly and through the holder. The manifold assembly and holder provide a flowpath through the lower manifold and the holder and the upper manifold. The holder has grooves on an internal surface thereof, and has slots through an external surface thereof. The grooves and slots are configured so that the fiber assemblies are able to be inserted through the and be supported by at least one of the grooves and slots. The slots comprise rounded edges on an outward-facing surface or the grooves comprise rounded edges on an inward-facing surface that is opposite the slots.

According to another embodiment of the invention, a method of culturing cells includes the step of providing a bioreactor, the bioreactor comprising: a reservoir container for holding a liquid medium; a manifold assembly, the manifold assembly comprising an upper manifold and a lower manifold, the lower manifold having a lower end extending into the reservoir container; a holder being contained within the manifold assembly, v holder holding a plurality of fiber assemblies that are suitable for cells to grow on; and a circulation system for causing the liquid medium to flow through the lower manifold and the fiber assemblies and the upper manifold. The method further includes the steps of seeding cells onto the fiber assemblies; and operating the circulation system under conditions appropriate for the cells to multiply into a plurality of cultured cells. The upper end of the duct comprises an overflow wall surrounded on its outside by a moat, a bottom of the being at a lower elevation than the top of the overflow wall, the upper end of the duct and moat being in contact with a pocket region. The pocket region is bounded by a structure that is connected to the duct, and the pocket region is isolated from fluid communication with an exterior of the pocket region. When the circulation system is operating, the liquid medium flows over the overflow wall within the pocket region and the liquid medium is in contact with gas that is contained in the pocket region, and the liquid medium overflows into the moat and is removed from the moat by the circulation system. The method also includes the step of harvesting the cultured cells from the bioreactor.

BRIEF DESCRIPTION OF THE DRAWINGS

Embodiments of the invention are further described but are in no way limited by the following illustrations.

FIG. 4A is a view of the closure piece of the screen holder, showing rounded entrances of slots in the screen holder.

FIG. 4B is another view of the closure piece of the screen holder, from a different perspective.

FIG. 4C is a view of a local region of the closure piece.

FIGS. 16A-16C show various views of the rotor.

DETAILED DESCRIPTION OF THE INVENTION

One phenomenon that is important in cell culture is the limiting distance for diffusion of nutrients and waste products during growth and maintenance of cells and tissue. Tissue in living organisms organizes itself so that cells are never separated by more than a certain distance from a blood vessel or transport path. The maximum distance for cells to be located away from a transport vessel such as a blood vessel is about several hundred microns. In the design of bioreactors, an important consideration is to provide a geometry in which cells are never separated from liquid medium by a distance greater than several hundred microns.

Another phenomenon that is relevant to isolated cells surrounded by liquid is motion of the cells through the liquid. The physical properties (density, viscosity) of a liquid culture medium typically similar to the physical properties of water. Cells that are loose in a liquid culture medium are slightly denser than the density of the liquid culture medium that surrounds them, which causes the cells to fall or sink downward under the influence of gravity. If a cell is considered to be a sphere moving in a viscous liquid, the situation is described by Stokes' Law. In this situation, the settling velocity, V, is given by $$V = (\rho_{cell} - \rho_{fluid}) * g * D^2 / (18 * \mu)$$

where D is the diameter of the sphere, $(\rho_{cell} - \rho_{fluid})$ is the difference in density between the sphere and the fluid, g is the acceleration due to gravity, and p is the viscosity of the fluid. This equation is valid for conditions of laminar flow.

Another consideration in cell culture is to provide a gaseous atmosphere in the incubator. which results dissolved gas in the cell culture medium, containing sufficient oxygen and also containing carbon dioxide in a desired concentration of about 20% and 5% respectively, and having a desired relative humidity such as about 95%. Yet another consideration is to provide a desired temperature such as approximately normal human body temperature, such as 37.0 C.

Another consideration in cell culture is the shear stress due to liquid that may be flowing past the cells that are attached to or in the process of attaching to a substrate or cell culture scaffold. It is desirable that such shear stress not exceed a certain value, so as not to dislodge the cells from the substrate or scaffold. It is believed to be especially important that the shear stress be small during the early stages of cell seeding in a bioreactor, when cells are still in the process of forming an attachment to the substrate or scaffold. For mesenchymal stem cells, it is believed to be desirable to keep the local shear stress under 0.1 Pa.

Herein, a first embodiment of the invention is described in which the cells are statically seeded onto the scaffolds that are in the form of screens, and the screens are then mounted inside a bioreactor, where liquid medium perfuses through the screens generally perpendicular to the screens.

Figure 1A:
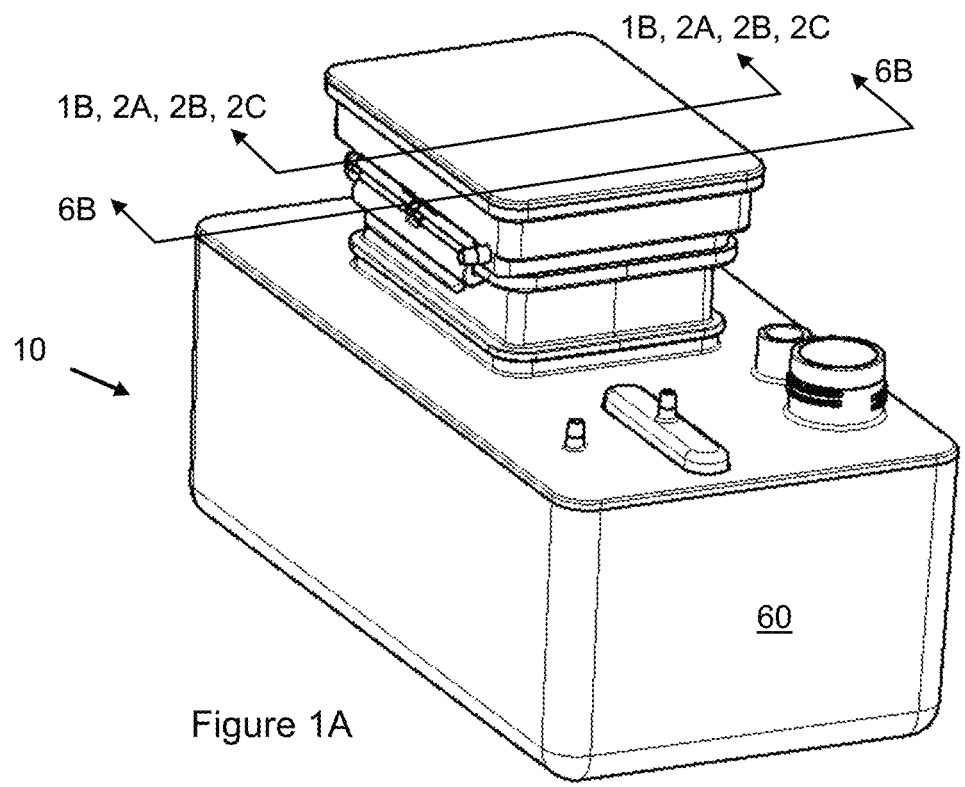
FIG. 1A shows an overall layout of some of the major components of a bioreactor of an embodiment of the invention.
Figure 1B:
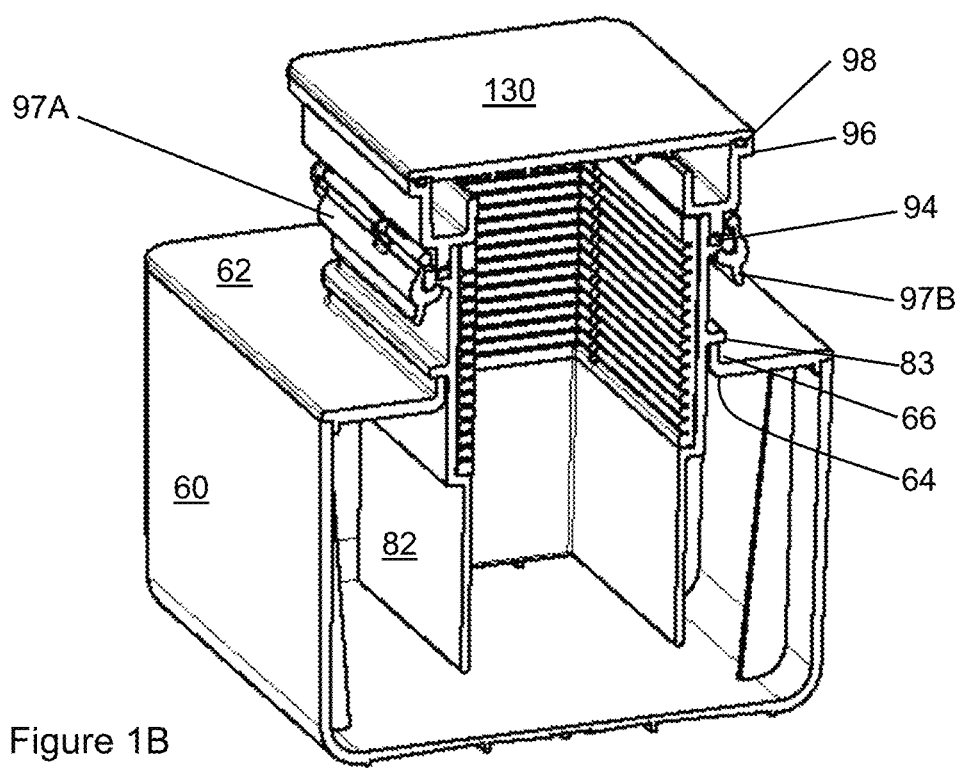
FIG. 1B shows the components of FIG. 1A in cross-section.

Referring now to FIGS. 1A and 1B, there is illustrated a bioreactor 10 of an embodiment of the invention. The bioreactor 10 may comprise a reservoir container 60 suitable to hold a desired quantity of a liquid medium. The bioreactor 10 may also comprise a reservoir cover 62 corresponding to reservoir container 60. The reservoir cover 62 may attach to the reservoir container 60 by a snap or other suitable fastener or attachment. The reservoir cover 62 may have an opening 64 therethrough suitable to receive a flow structure extending through the opening 64 and suitable to extend below a surface of liquid medium in the reservoir container 60. The flow structure may comprise, as illustrated, various pieces that fit together and may receive or enclose a screen holder 200. The screen holder 200 in turn may hold screens 300 upon which cells reside and grow. The array of screens 300 can be referred to as a culture structure.

Upper Manifold and Lower Manifold

Figure 2A:
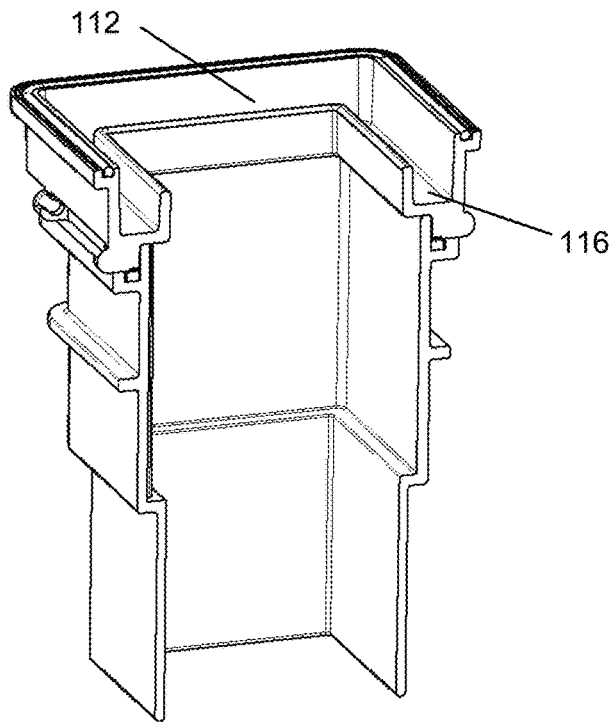
FIG. 2A shows an assembly, in cross-section, comprising the lower manifold and the upper manifold.
Figure 2B:
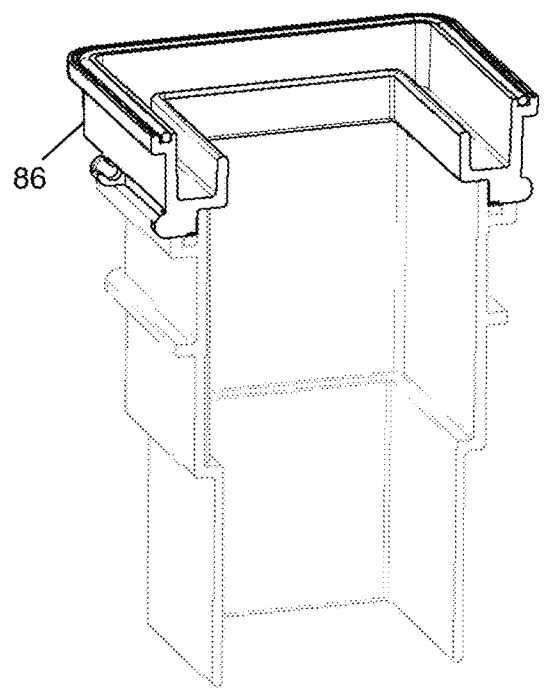
FIG. 2B shows the same assembly as FIG. 2A, with the upper manifold highlighted.
Figure 2C:
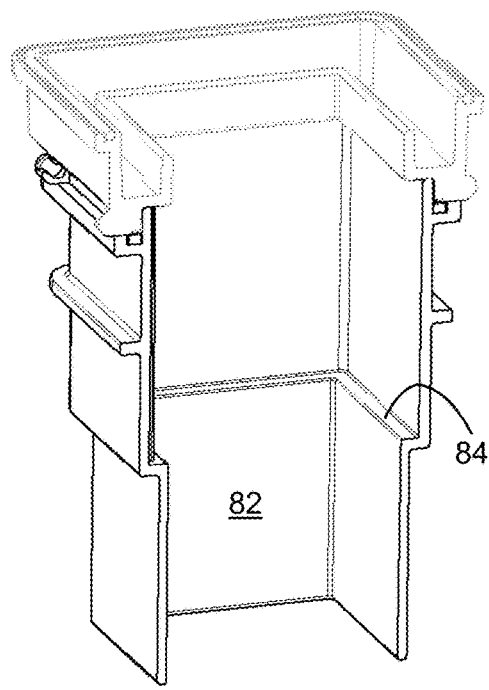
FIG. 2C shows the same assembly as FIG. 2A, with the lower manifold highlighted.
Figure 3A:
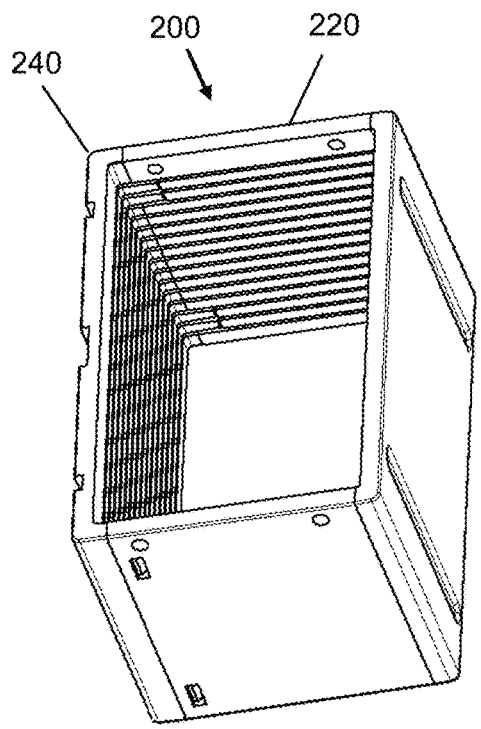
FIG. 3A is a three-dimensional view showing a screen holder, without screens.
Figure 3B:
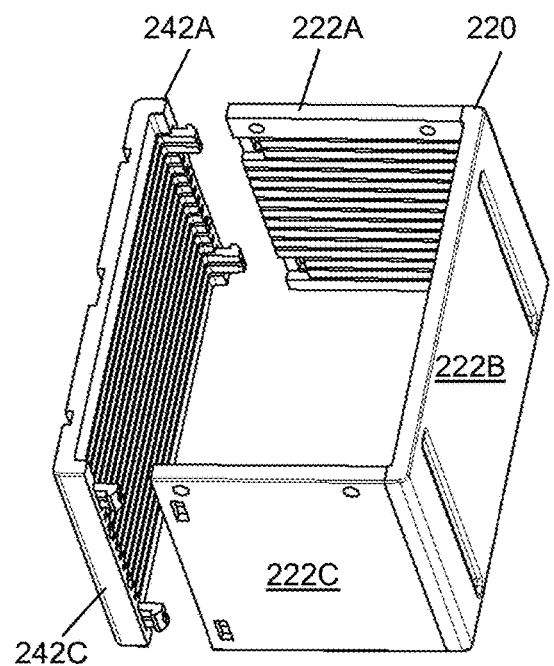
FIG. 3B is a three-dimensional view showing the screen holder of FIG. 3A, exploded.
Figure 3C:
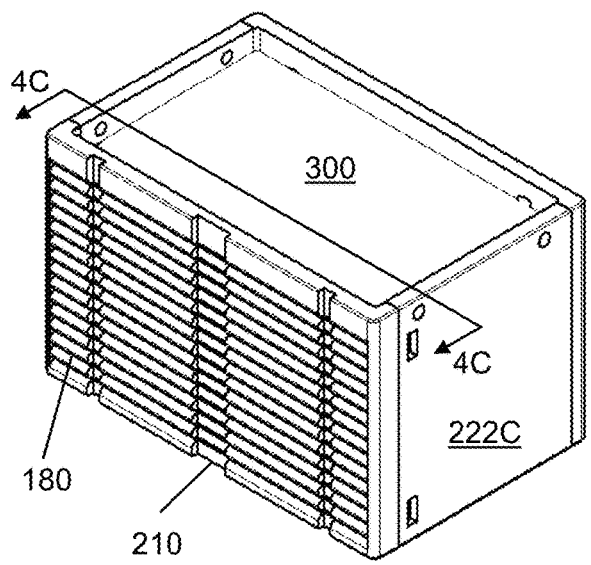
FIG. 3C is a three-dimensional view showing the screen holder with screens in it. For clarity of illustration, one part of the screen holder is colored differently from the other part.
Figure 3D:
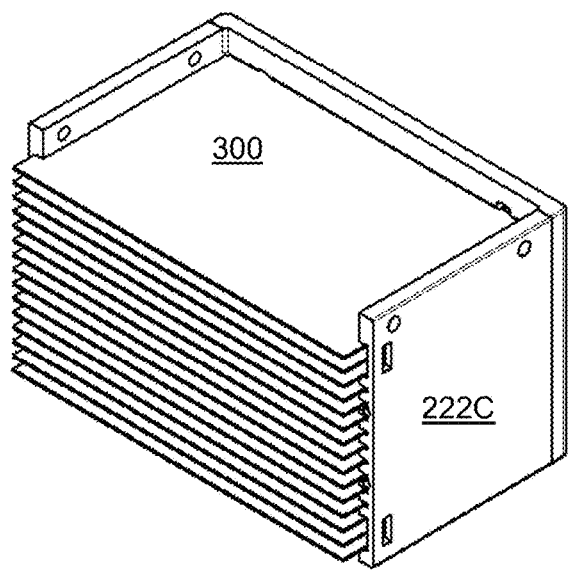
FIG. 3D is a three-dimensional view showing the screen holder of FIG. 3C with one part of the screen holder missing in order to better show the screens.
Figure 3E:
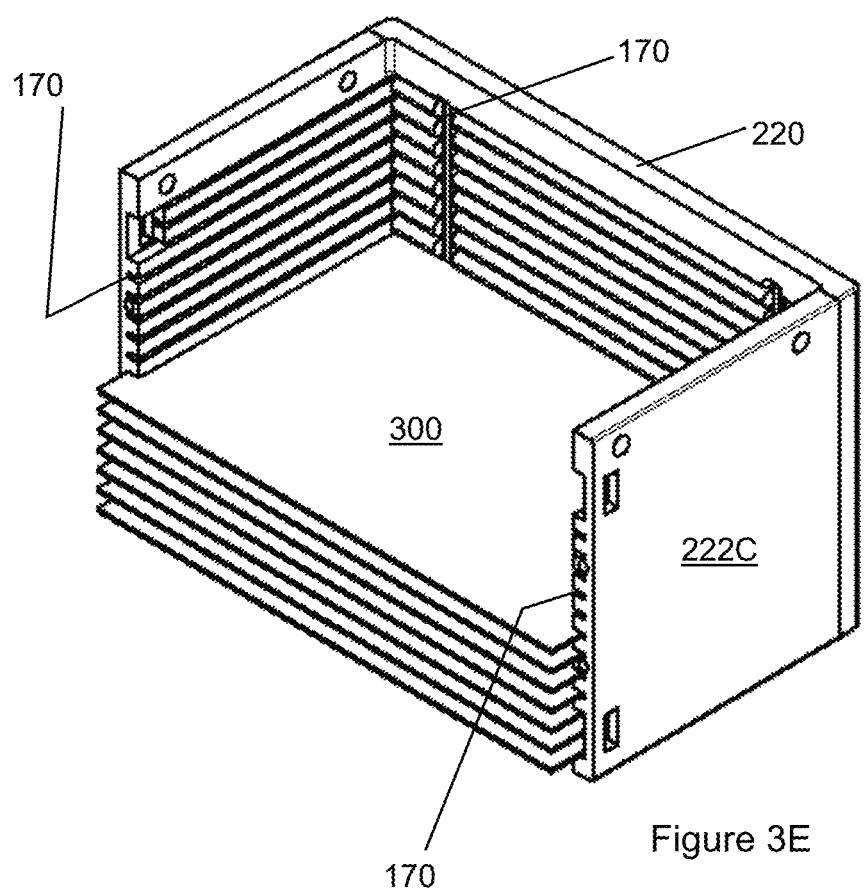
FIG. 3E is a three-dimensional view showing the screen holder of FIG. 3D with some of the screens missing.

Referring more specifically to FIGS. 2A, 2B and 2C, the flow structure may comprise a manifold assembly that comprises lower manifold 82 and an upper manifold 86. Lower manifold 82 and an upper manifold 86 may fit together with each other, and in combination may surround and enclose screen holder 200. Lower manifold 82 may extend downward into reservoir container 60 sufficiently so that the bottom end of lower manifold 82 may extend below a desired level of liquid medium that is stored in the reservoir container 60.

The interior of lower manifold 82 may be generally close-fitting with respect to the exterior of screen holder 200. Lower manifold 82 may have a ledge 84. Screen holder 200 may rest upon ledge 84, but screen holder may also be able to move slightly upward in the vertical direction.

Upper manifold 86 may be suitable to fit together with lower manifold 82. Upper manifold 86 may define an internal passageway therethrough that is in fluid communication with the interior of lower manifold 82 and with the interior of screen holder 200 if screen holder 200 is present inside lower manifold 82. Upper manifold 86 may have an internal that is of similar shape to the interior of lower manifold 82. The interior of upper manifold 86 and the interior of screen holder 200 may be of similar or identical shape and dimensions so that changes of cross-sectional flow area and changes of flow direction are small or non-existent as flow goes through lower manifold 82 and then through screen holder 200 and then through upper manifold 86.

Upper manifold 86 may have, above the location where it interfaces with lower manifold 82, an upper end that is weir or overflow wall 112. Weir 112 may be a generally horizontal edge defining a perimeter of the passageway through upper manifold 86. When liquid is present and flowing in the system with an air space in the upper portion of upper manifold 86, weir 112 may define a liquid level of liquid inside upper manifold 86 and related components. External of weir 112 may be a moat 116 may have a bottom that is at a lower elevation than the top of weir 112. Moat 116 may be suitable to receive and contain liquid that overflows weir 112. Moat 116 may further have a sump 118, which may be a localized depression that is smaller than moat 116 and is at a lower elevation than other parts of moat 116. There may further be provided, in fluid communication with sump 118, an exit passageway by which liquid medium may exit to other parts of a fluid circuit.

Upper manifold 86 may engage with lower manifold 82 in a slideable manner that is guided by a feature of upper manifold 86 being parallel to, of similar shape, and of similar dimensions but allowing enough looseness for motion, with respect to a corresponding feature of lower manifold 82. As illustrated, the feature of upper manifold 86 is located outwardly with respect to the feature of lower manifold 82. Upper manifold 86 may have a contact with lower manifold 82 that limits the motion of upper manifold 86 toward lower manifold 82, forming a stop constraint. Alternatively, it is possible that motion of upper manifold 86 and lower manifold 82 toward each other could be stopped when an appropriate surface (which may be flat) of upper manifold 86 makes contact with an upper surface of screen holder 200, and correspondingly a lower surface of screen holder 200 makes contact with an appropriate surface (which may be flat) of lower manifold 82.

There may also be provided a top cover 130 that covers the top of upper manifold 86. Top cover 130 may be at least approximately a flat plate. If desired, top cover 130 may have stiffening ribs. Top cover 130 may be permanently joined to upper manifold 86 and, there may also be provided a seal between top cover 130 and upper manifold 86. It would alternatively be possible if desired to provide some form of fastener connecting top cover 130 and upper manifold 86.

As illustrated, opening 64 through reservoir cover 62 may have a raised edge or lip 68 surrounding it, and lower manifold 82 may have a flange 83 surrounding lower manifold 82 on its exterior. Flange 83 may rest upon raised edge or lip 68 to define a spatial relationship between lower manifold 82 and reservoir cover 62. Raised edge or lip 68 may provide that if any condensation of liquid water occurs on reservoir cover 62, and if such condensate is not sterile, such condensate can be prevented from dripping into reservoir container 60. Such condensate may be confined to the top (external) surface of reservoir cover 62. Various designs of such lip are possible.

Seals and Clamps

Lower manifold 82 may have a lower manifold seal groove 92 that is suitable to contain a compressible seal 94 for creating a seal between lower manifold 82 and upper manifold 86. This compressible seal 94 is illustrated as having a shape, in cross-section, that is rectangular with deformable triangular fingers on one surface. Of course, other cross-sectional shapes are also possible. Preload between upper manifold 86 and lower manifold 82 may be created by clamping devices, which may be over-center type clamping devices. Two such clamping devices 97A, 97B are illustrated. When the described stop situation is reached based on position of upper manifold 86 and lower manifold 82 relative to each other, compressible seal 94 may occupy a compressed configuration.

Upper manifold 86 may have an upper manifold seal groove 96 that is suitable for holding a compressible seal member 98 for creating a seal between upper manifold 86 and top cover 130. This compressible seal member 98 is illustrated as being a typical O-ring. Preload between top cover 130 and upper manifold 86 may be created by snaps (not illustrated), clamps (not illustrated) or any other appropriate design features. Another possibility is that top cover 130 can be permanently joined to upper manifold 86 such as by adhesive.

Screen Holder

In an embodiment of the invention, the screens 300 may be held by a screen holder 200. The screen holder 200 is illustrated in FIGS. 3A-3E and FIGS. 4A-4C. Screen holder 200 may hold a desired number of screens in a desired spaced position and orientation. The screen holder 200 illustrated in FIGS. 3A-3E and FIG. 4A-4C holds 15 screens 300. It may be desirable that the number of screens be not much larger than approximately 15 in order to avoid creating gradients of oxygen concentration in the liquid medium during operation of the bioreactor.

In general, screen holder 200 may surround a hollow interior space and may be any of various shapes such as round, rectangular, etc. As illustrated, the screen holder 200 (on both its both interior and its exterior) has the general shape of a rectangle with rounded corners. The screens 300 held by the illustrated screen holder 200 are rectangular. For sake of convenience in description, screen holder 200 is described here using directional designations such as front and back, sides, and horizontal and vertical, which generally correspond to their orientation or position as illustrated in the assembled bioreactor 10. However, it may be understood that these directional designations are somewhat arbitrary.

When screens 300 are in place in screen holder 200, there may be a desired amount of space in the vertical direction between a screen 300 and its nearest neighbor screen. In the bioreactor 10 as illustrated, the flow of the liquid medium can be generally perpendicular to the flat surface of screens 300, flowing through the open spaces in the screen 300.

A cell culture region could contain, for example, approximately 15 such screens 300 spaced apart from each other by a sufficient distance so that the screens do not touch each other and some sideways flow of liquid medium is possible if necessary.

Screen holder 200 could be of a hollow simple shape some of which forms a complete perimeter, with the shape being a shape such as round or rectangular (possibly with rounded corners). In general, it is possible that screen holder 200 could be made as a single piece, such as by an additive manufacturing process. However, perhaps more typically screen holder 200 could be made out of two pieces, such as two pieces of molded plastic, that join together with each other. It is illustrated that screen holder 200 is made of two inter-engaging pieces. The screen holder 200 may comprise a three-sided piece 220 and a closure piece 240 that is engageable with the three-sided piece 220. The three-sided piece 220 may comprise, in sequence, a first side segment 222A, a rear segment 222B and a second side segment 222C opposed to the first side segment 222A. The closure piece 240 may comprise at least one segment, which may be considered a front segment 242B. As illustrated, the closure piece 240 may additionally comprise a first side segment 242A and a second side segment 242C. Thus, in sequence, there is a first side segment 242A, a front segment 242B and a second side segment 242C. The first side segment 242A may be engageable with the first side segment 222A, and the second side segment 242C may be engageable with the second side segment 222C. However, it is also possible that the closure piece 240 might comprise only a front segment 242B. As illustrated, front segment 242B and rear segment 222B are substantially parallel to each other, and first side segment 222A and second side segment 222C are substantially parallel to each other and first side segment 242A and second side segment 242C are substantially parallel to each other. However, other spatial relationships are also possible.

The engagement features may comprise deformable tabs 800, and further may comprise an opening 224A in first side segment 222A and a similar opening 224C in second side segment 222C, with the openings 224A and 224C being appropriately designed to engage with tabs 800. The tabs 800 may be elastically deformable between an engagement position as illustrated, and a release position in which the deformable tabs 800 are bent inward sufficiently to create disengagement. The tabs 800 may comprise living hinges, and it is further possible that elasticity elsewhere in the closure piece 240 may also contribute to changes of dimension or shape so as to permit or assist in achieving disengagement.

Screen holder 200 may have an upper edge and a lower edge that may be flat, and which may be parallel to each other.

Slots and Grooves in Screen Bolder, and Rounded Edges Near Slots and Grooves

The screen holder 200 may comprise various grooves and slots that define locations of screens 300 and provide mechanical support for screens 300. As illustrated, screen holder 200 is able to hold 15 of the screens 300, but of course other numbers of screens 300 are also possible. The spacing distance between screens 300 may be chosen from a combination of considerations such as patterns of fluid flow between screens 300, and desired overall packing density of cells in the cell culture region of bioreactor 10.

If screen holder 200 were made as a single piece (similar to what is illustrated but with the three-sided piece 220 and the closure piece 240 joined together), it would be possible to insert and remove screens 200 into or from screen holder 200. This can be done from a sideways direction.

In the screen holder 200 as described and illustrated, it is possible to insert and remove screens 300 into or from screen holder 200 when three-sided piece 220 and closure piece 240 are already assembled to each other, without disassembling those pieces from each other. This can be done from a sideways direction. As illustrated, first side segment 222A has grooves 170, and second side segment 222C has grooves 170. Rear segment 222B has grooves 170. Front segment 242B has slots through which screens 300 may pass without disassembly of screen holder 200. The grooves 170 may be substantially co-planar with each other and may have similar or identical dimensions to each other in the vertical direction. Slots 180 may be parallel to or coplanar with at least some of grooves 170. The vertical dimensions and elevations of slots 180 may be identical to those of grooves 170, although it is sufficient if the vertical dimensions and elevations are simply generally similar to each other. These various features may combine and interact so that when screen holder 200 is assembled, it is possible for screens 300 to be slid into place through slot 180 and to be supported by grooves 170, as well as by slot 180. The desired spacing or separation between screens 300 is maintained by the material of screen holder 200 near grooves 170, and by the material of screen holder 200 (ligaments) that exist between slots 180.

As illustrated, closure piece 240 has three sides, with two of the sides 242A, 242C being short. One side wall of screen holder 200 comprises both first side segment 222A and first side segment 242A, and similarly the other side wall comprises both second side segment 222C and second side segment 242C. As illustrated, even tabs 800 contain grooves that are continuous with grooves 170 in the corresponding adjacent side segments. However, it can be understood that various other designs are also possible.

As illustrated, grooves 170 in first side segment 222A and first side segment 242A are substantially sharp-edged. The same is true for grooves 170 in second side segment 222C and second side segment 242C. However, it can be understood that other geometries are also possible.

On a front portion of the screen holder 200, the separators or ligaments of remaining material may be such that there are rounded edges face generally exteriorly of the screen holder 200. This can be helpful in guiding screens 300 into slots 180 during initial insertion of the screens 300 into slots 180. The rounded edges may be hemicylindrical. Such rounded edges can also be helpful in guiding screens 300 into slots 180 if it happens that any of the screens 300 are not perfectly planar, such as being slightly warped out-of-plane.

At a rear portion of the screen holder 200, separators between individual screens 300 may be such that there are rounded edges face generally toward the interior of the screen holder 200. This can be helpful in guiding screens 300 into desired positions when screens 300 are being inserted into screen holder 200, such as near the end of the insertion process. The rounded edges may be hemicylindrical. The rounded edges may be hemicylindrical. Such rounded edges can also be helpful in guiding screens 300 into grooves 170 if it happens that any of the screens 300 are not perfectly planar, such as being slightly warped out-of-plane.

The separators at the front portion of the screen holder 200 may define slots through which the screens 300 may pass. The separators at the rear portion of the screen holder 200 may define grooves into which the screens 300 may enter but through which it is impossible for screens 300 to pass.

In the case of both the rounded edges of the slots 180 and the rounded edges of grooves 170, a hemicylindrical curvature is only one of various possible curvatures. A fillet having some other desired radius is also possible. Such radius could be either less than or greater than the radius of the hemicylinder. Other shapes of curves are also possible. Variation of curvature along the length of the slot 180 or groove 170 is also possible.

Design of Screens

Figure 5A:
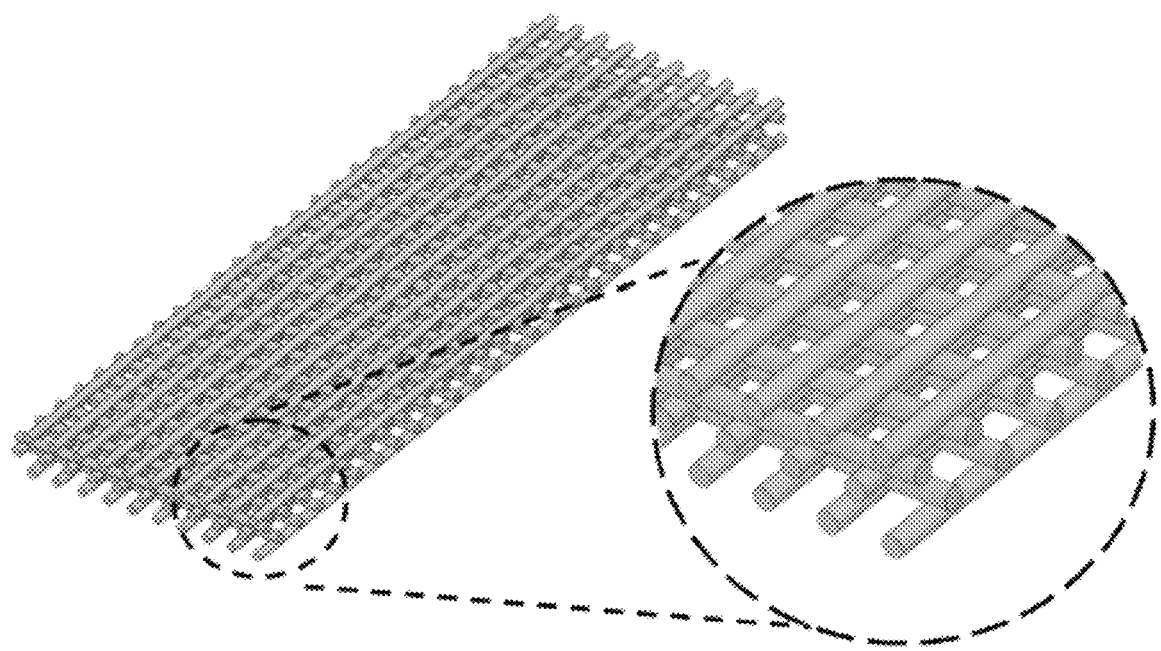
FIG. 5A shows a screen made according to an embodiment of the invention.
Figure 5B:
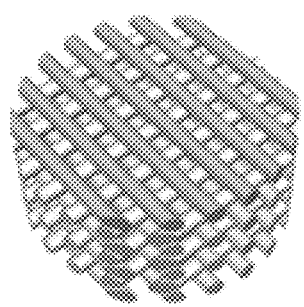
FIG. 5B shows a closer view of a similar screen.

In embodiments of the invention, and referring now to FIGS. 5A-SD, the bioreactor 10 may have, within the culture region, an array of screens 300, which serve as tissue scaffolds for cells such as anchorage-dependent cells to grow upon. The individual screens 300 themselves may comprise a number of layers of fibers 400, with the fibers 400 having orientations that are perpendicular to the orientations of fibers in an adjacent layer. In a particular embodiment of the invention, the number of layers of such fibers 400 in an individual screen 300 may, for example, be four or five or six layers.

Figure 5C:
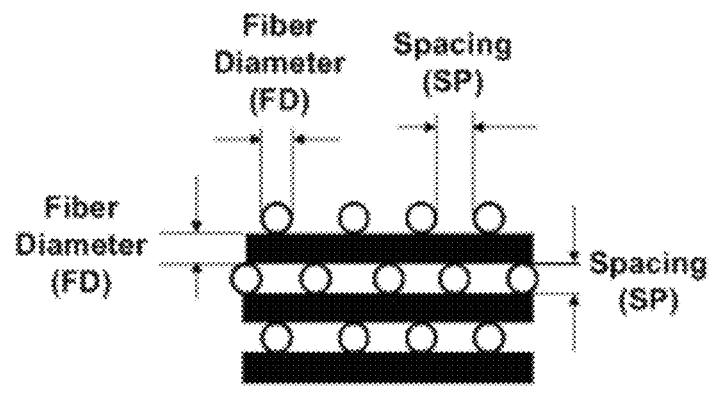
FIG. 5C illustrates spacing parameters of the screens such as those in FIGS. 5A and 5B.

Typical dimensional parameters of such screens 300 could be a fiber diameter of 150 microns and a fiber spacing (as defined in FIG. 5C) of 200 microns, with that dimension referring to the distance from an edge of one fiber to the nearest edge of the nearest fiber in the same plane. Fibers 400 in one layer may be staggered relative to fibers 400 that are parallel to them and are located in a different layer of the screen 300, or alternatively there does not have to be staggering. The fibers 400 may be spaced apart from each other by appropriate distances such that during initial cell seeding, the cells deposit on fibers 400 and do not touch cells on adjacent fibers 400. However, the spacing of the fibers 400 may be such that after some number of cell multiplications, cells growing on nearby fibers 400 may contact or grow against each other (a situation known as confluence).

Figure 5D:
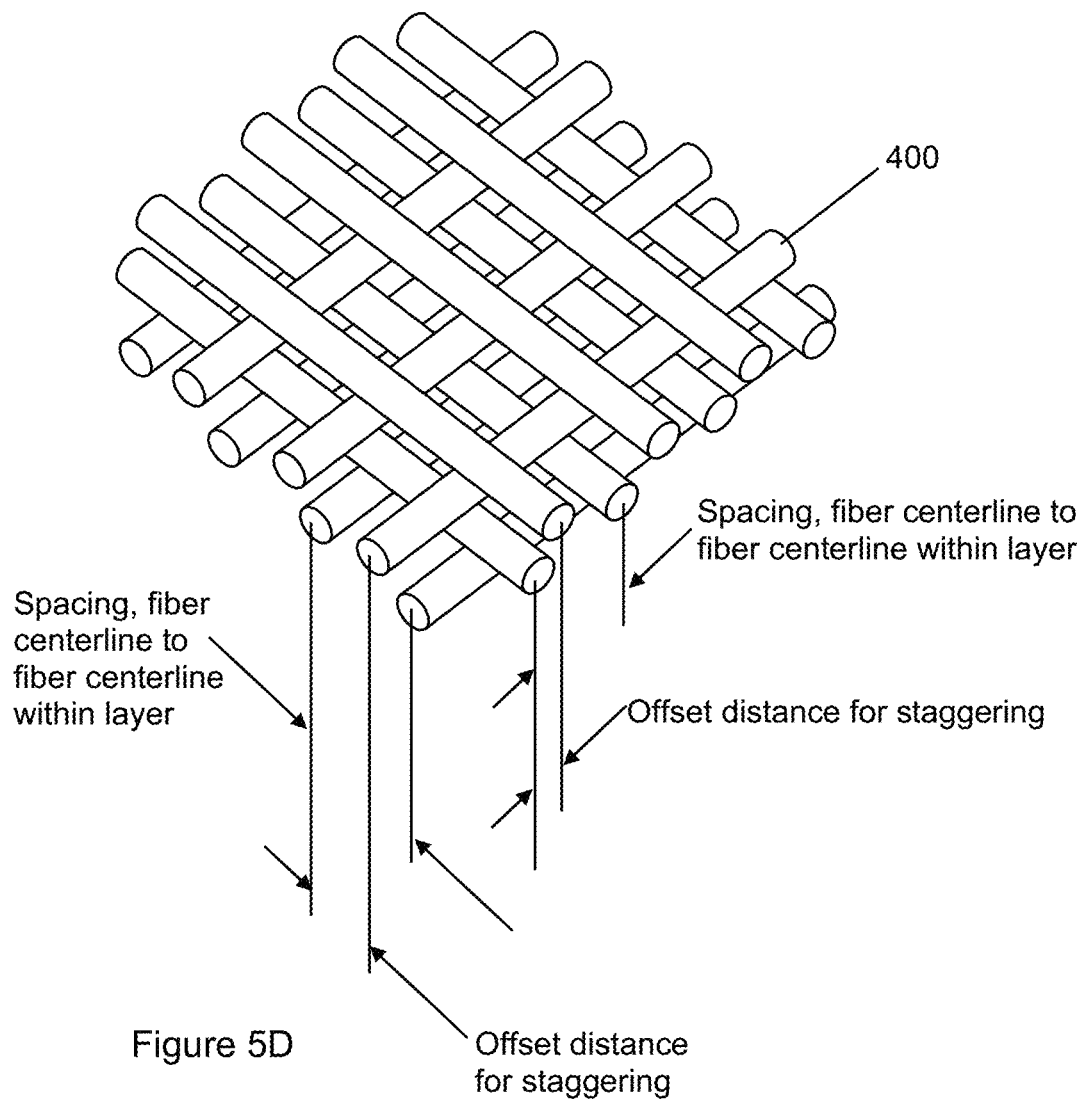
FIG. 5D illustrates more specifically the placement of fibers within a screen, and their staggering.

More particularly, the fibers 400 may exist in two mutually perpendicular directions and may be staggered in both of those two mutually perpendicular directions. This is further illustrated in FIG. 5D. Each screen may comprise a plurality of fibers forming a first layer having parallel fibers oriented in a first direction and may comprise a second layer having a plurality of parallel fibers oriented in a second direction that is perpendicular to the first direction, the fibers in the second layer being joined to the fibers in the first layer. At least some of the screens comprise a plurality of fibers, and within an individual one of the screens, the fibers are arranged in sequence in at least first, second, third and fourth layers, the fibers within each of the layers being generally parallel to each other, wherein fibers in the first layer are generally parallel to fibers in the third layer and fibers in the second layer are generally parallel to fibers in the fourth layer, and wherein when viewed perpendicular to a flat surface of the screen, fibers of the third layer are located non-aligned with fibers of the first layer and fibers of the fourth layer are located non-aligned with fibers of the second layer. More specifically, with respect to this viewing direction, the fibers may be located midway between the parallel fibers that they are not aligned with. Such configuration can help to prevent cells from falling through the screen, especially during initial seeding, while still providing space for liquid medium to occupy and flow through, and providing space for cells to grow into as the cells multiply.

A screen 300 may have a particular number of layers, such as four layers, with media available at both surfaces of the four-layer construct, for contacting cells, and media also available in openings that exist between layers. It is believed that all of the features of this situation more closely resemble what occurs in natural tissues, which can be termed a three-dimensional environment. It is believed that the three-dimensional situation of embodiments of the invention is more conducive to cell multiplication and expansion than is a two-dimensional environment. However, it is not wished to be limited to this explanation.

The screens 300 may be formed by a programmed deposition of heated filaments of polymer, similar to what is described in commonly-owned U.S. Pat. No. 8,463,418. The polymer may be a suitable biocompatible polymer such as polystyrene. The screen 300 as described is non-woven. Alternatively, screen 300 may be woven if desired. The overall shape of the screen 300 may be flat and rectangular.

In some prior art cell culturing techniques such as Petri dishes, a layer of cells grows on a flat surface and experiences an environment that is essentially two-dimensional. Even if there is adequate supply of nutrients and removal of waste products in this situation, such a two-dimensional environment is by inherently different from the environment in which cells naturally grow, which is a three-dimensional environment.

In embodiments of the invention, cells seed by attaching onto individual fibers of the screen. The fiber-to-fiber dimension of the screen may be large enough that when isolated cells initially attach to the fibers, at least some of the cells generally do not touch other cells. After cells have multiplied, and perhaps created several layers of cells where initially only one layer of cells was attached to a fiber, it is possible that the outermost cells may still be independent of the next fiber or it is possible that some of the new cells may touch other cells that are attached to other fibers, i.e., some bridging of fibers may occur (referred to as confluence). In embodiments of the invention, a screen may have a particular number of layers of fibers, such as four layers. with media available at both surfaces of the four-layer construct, for contacting cells. At any rate, it is believed that all of the features of this situation more closely resemble what occurs in natural tissues, which can be termed a three-dimensional environment. It is believed that the three-dimensional situation of embodiments of the invention is more conducive to cell multiplication and expansion than is a two-dimensional environment. However, it is not wished to be limited to this explanation.

A cell culture region could contain, for example, approximately 10 to 15 such scaffolds spaced apart from each other by a sufficient distance so that the screens do not touch each other and liquid can flow between the scaffolds.

In terms of biological parameters, a screen used with an embodiment of the invention may have an area (length dimension*width dimension) of about 7000 $mm^2$, and the portion of that screen exposed to perfusion (excluding the edges that are in grooves or slots) may have an area of about 6300 $mm^2$. This screen may be formed of four layers of fibers, with the layers alternating in direction as described elsewhere herein. On such a screen there may be deposited an initial seeding of about 800,000 cells, so that if 12 screens are used, the population of seeded cells is 9.6 million cells. At the end of culturing, that cell population has expanded to about 250 million cells. Flow of liquid media speed based on the empty space in the screen, for dynamic culturing, can be approximately 2 cm/min. It is believed that a flow velocity of 1.6 mm/sec, based on the empty space for passage of liquid through the screen, will produce a maximum shear stress, at the edge of a fiber in the screen, of 0.1 Pa, and it is believed to be desirable that for mesenchymal stem cells the shear stress should stay below this value.

Dimensional Considerations Affecting Flow

In embodiments of the invention, the general direction of flow of the liquid medium may be perpendicular to and through the screens 300, which as illustrated is vertically upward.

In embodiments of the invention, cells seed by attaching onto individual fibers 400 of the screen 300. The fiber-to-fiber dimension of the screen 300 may be large enough that when isolated cells initially attach to the fibers 400, they generally do not touch other cells. After cells have multiplied, and perhaps created several layers of cells attached to a fiber 400 where initially only one layer of cells was attached to a fiber 400, it is possible that the outermost cells may still be out of contact with cells that are attached to the nearest-neighbor fiber 400, or it is possible that some of the new cells may touch other cells that are attached to other fibers 400, i.e., some bridging between fibers (confluence) may occur. Even if confluence does not occur, after additional cells have grown, the open space for passage of liquid medium through the screen is smaller than it was at the start of culturing.

In embodiments of the invention, the screens 300 may fit within grooves 170 or slots 180 of screen holder 200 with a slight degree of looseness. This is so that screens 300 can be easily inserted into or removed from the grooves 170 and slots 180. For example, a total height of a screen 300 may be 600 microns, while the vertical dimension of a groove 170 or slot 180 may be 1 millimeter. This leaves a gap, in the vertical direction, between the screen 300 and the groove 170 or slot 180. In the horizontal direction, in a side-to-side direction, the dimensions of the screen 300 may be slightly smaller than the horizontal dimensions defined by the base of a groove 170 on one side of the screen holder 200 to the base of the groove 170 on the other side of screen holder 200. In the horizontal direction, in the front-back direction, the location of the screen 300 may be determined by two limiting structures between which the screen 300 may fit with a slight degree of looseness. One of those structures may be the interior wall of the lower manifold 82. The other structure may be the inward-facing extreme of boss 216. In the front-back direction, the screen may be slightly smaller, at least at the location of the boss 216, than the distance between the boss 216 and the opposed inward-facing surface of lower manifold 82. Alternatively, it is also possible that some features of screen holder 200 could be involved in determining the position of screen 300.

The following forces can act on a horizontally-oriented screen during flow through the screen: the weight of an individual screen when submerged in the liquid medium; and the drag force due to flow of the liquid medium (which can be approximated as the pressure difference across the screen holder, divided by the number of screens). This force balance will determine whether the screens sit on the lower edge of the groove, or are pushed upward and pinned against the upper edge of the groove, or float somewhat unstably in between those other two positions. At least one of these quantities, i.e., the pressure drop, can vary during the course of culturing, as the screens become more crowded with cells.

At the same time, it is desired that most of the flow of liquid medium go through the openings in the screen 300.

Figure 6A:
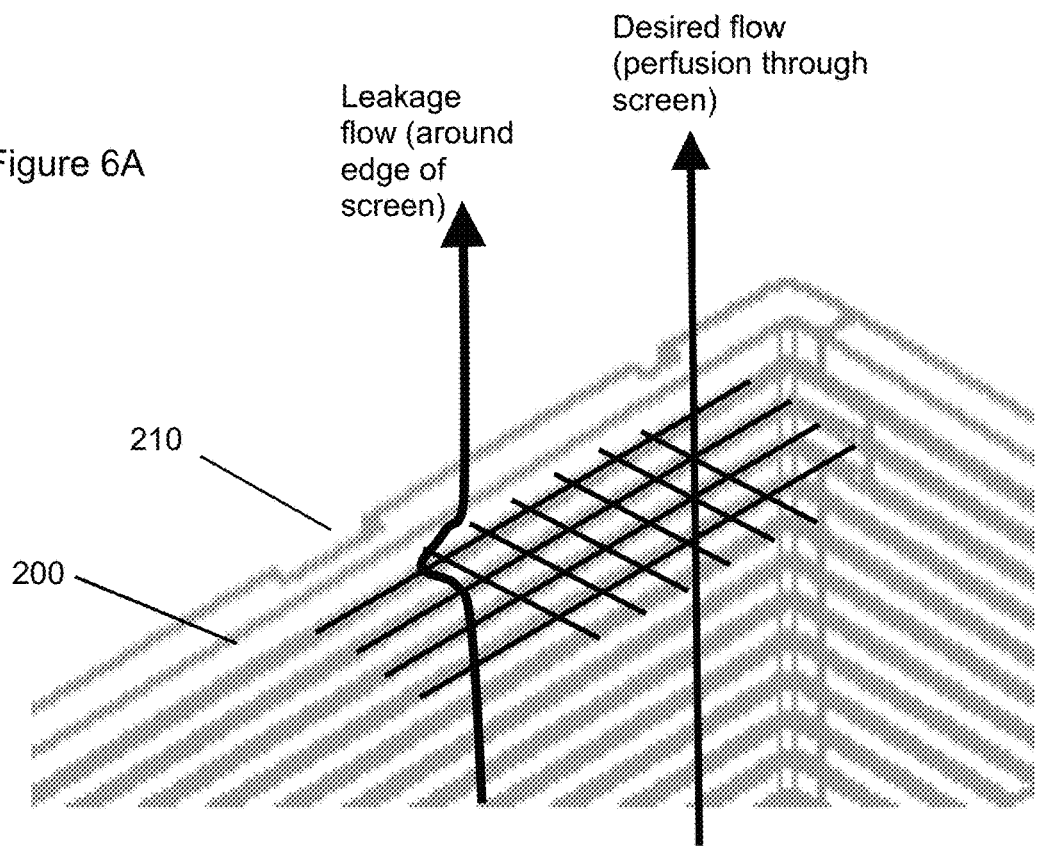
FIG. 6A illustrates a possible leakage flowpath.

In the described stack of screens 300 and within the described screen holder 200, there are various possible local flowpaths of the liquid medium. In much of the screen 300, there is open space between fibers 400 through which the liquid medium can flow. Prior to the seeding of cells onto the screen 300, the dimensions of the minimum flow area for a particular opening between fibers 400 can be approximated as the inter-fiber spacing distance by the inter-fiber spacing distance. Also, prior to the seeding of cells, when the screen is mounted into the screen holder 200, there is a possible flow path at the edges of the screen 300. Such flowpath is illustrated in FIG. 6A. Flow in such flowpath may be influenced by local dimensions such as the inter-fiber spacing distance, and the gap in a horizontal direction between the screen 300 and the screen holder 200, and the gap in a vertical direction between the screen 300 and the screen holder 200. However, for simplicity of discussion, it can be assumed that the area for leakage flow, for one space between fibers 400, is the inter-fiber spacing distance by the inter-fiber spacing distance.

It may be of interest to compare the desired flowrate to the leakage flowrate, in the form of a ratio of those two quantities. If the screen external dimensions are assumed for simplicity to be square with a side length of L, the number of cells along the perimeter would be $4*L/\Delta$, where $\Delta$ is the inter-fiber spacing distance. The total flow area of all such leakage paths then would be $(4*L/\Delta)*\Delta^2$, or $4*L*\Delta$. In the same situation, for desired flow, the total flow area through the screen is $L^2*\Delta^2$. The ratio of desired flow area to leakage flow area is $L^2*\Delta^2/(4*L*\Delta,)$, or $L/(4*\Delta,)$, or $0.25*(L/\Delta)$. For the desirable goal of having most of the flow go through the openings in the screens 300 rather than through leakage paths, this incentivizes having a screen 300 having many cells within the length of a side of the assumed square shape. For example, the system may be designed so that a leakage path comprising a gap between an individual one of said screens and said screen holder, has a cross-sectional flow area that is less than 10%, or less than 2%, of a total flow area through all passageways through said individual one of said screens.

A further level of detail is to assume that the open spaces in the main part of the screen 300 become smaller as time goes on and the cell population increases. It can be assumed that they come to a value that may be called $\Delta_{crowded}$. It is then necessary to make an assumption about the open spaces at the edge of the screen 300. It may be assumed that the open spaces at the edge do not change their dimension, and their dimension remains at what may be called $\Delta_{edge}$. Then, the above ratio of flow areas becomes $L^2*\Delta_{crowded}^2/(4*L*\Delta_{edge})$, or $0.25*L*\Delta_{crowded}^2/\Delta_{edge}$. This is of course subject to assumptions especially concerning the open dimension at the edge, i.e., $\Delta_{edge}$, but in general as $\Delta_{crowded}$ becomes smaller, the ratio of flow area for desired perfusion flow, divided by flow area for leakage flow can become smaller than it was for the empty screen 300.

Another consideration affecting the design of a bioreactor may be the stiffness of the screens 300 against bending. When screens 300 are in the bioreactor and are supported by screen holder 200, they are subjected to gravity (either with or without buoyancy effects depending on whether liquid medium is or is not present), and they also are subjected to flow forces if the liquid medium is moving. Any such forces could deform the screen 300 out-of-plane. It is desirable that the screens 300 not deform so much that they touch each other or come loose from screen support 200. Stiffness of a screen 300 can be characterized by its deformation in bending in a simple bending geometry in which two opposed edges are supported as simple supports and the other two edges are unsupported. For the described screens, which had a dimension along the direction of bending of about 100 mm, and a transverse dimension of about 60 mm, a weight of 14.5 grams applied at the center of the span caused a deflection of 3.1 mm. The screen may be designed to be at least as stiff in bending as the just-described bending stiffness. When the screen is supported at four edges rather than the just-described two edges, it will deflect less than in the just-described measurement.

Start-Up Procedure

Figure 6B:
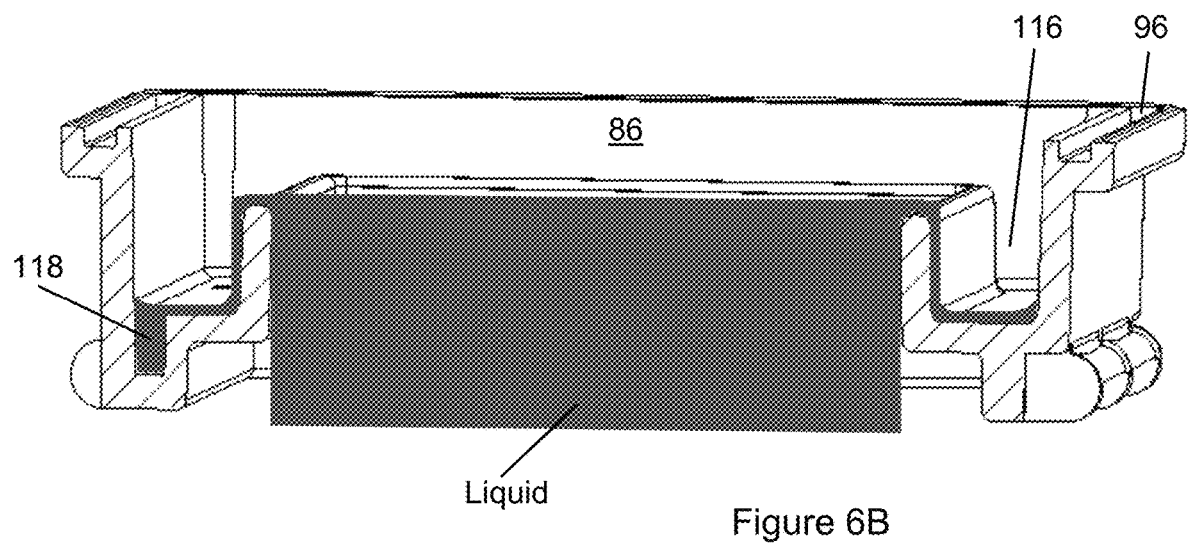
FIG. 6B illustrates places where liquid medium is present during typical operation of the system.
Figure 7A:
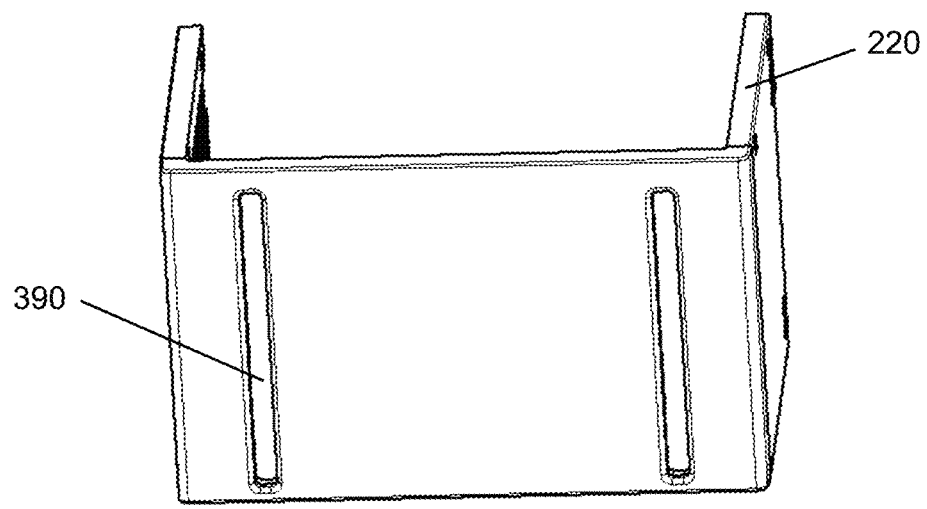
FIG. 7A illustrates the three-sided piece that is part of the screen holder, so as to illustrate positioning slots.
Figure 7B:
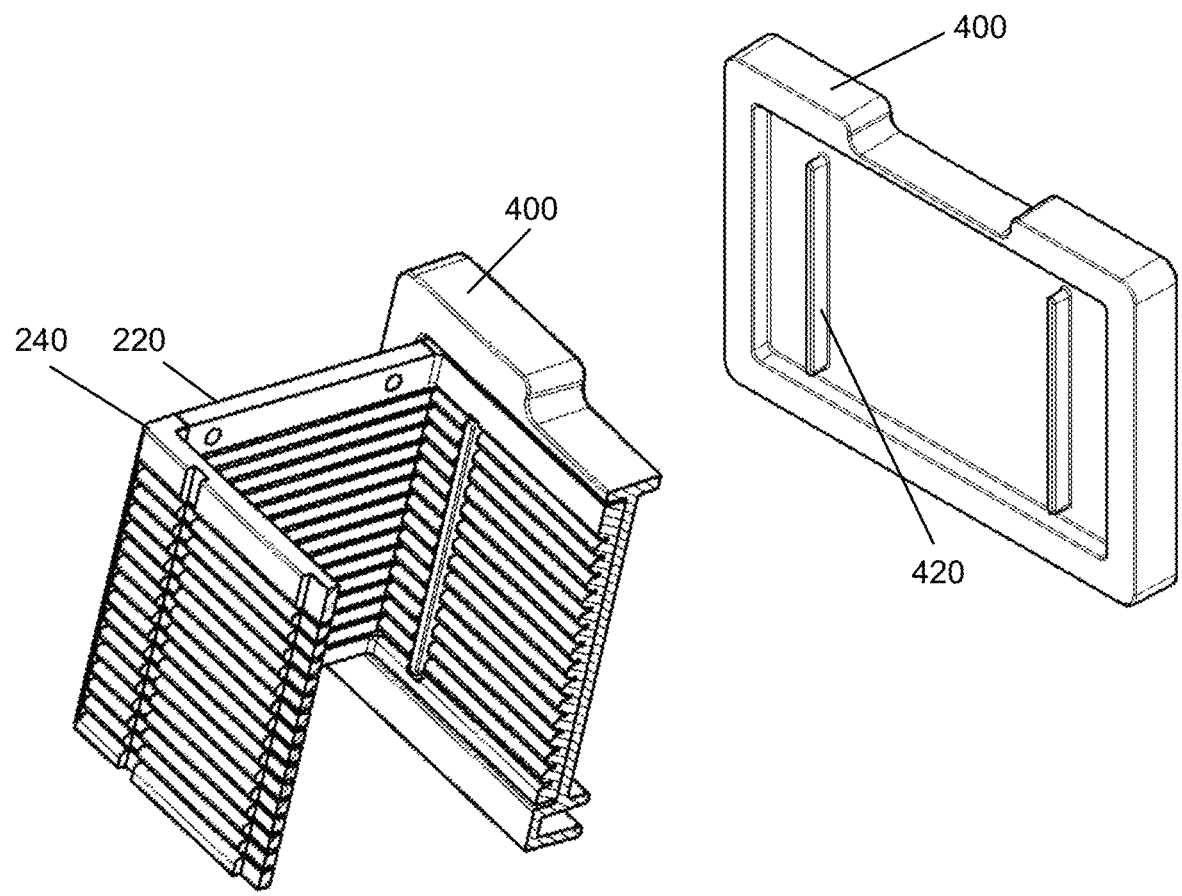
FIG. 7B is a cutaway view illustrating the three-sided piece of FIG. 7A, together with a pusher accessory.
Figure 7C:
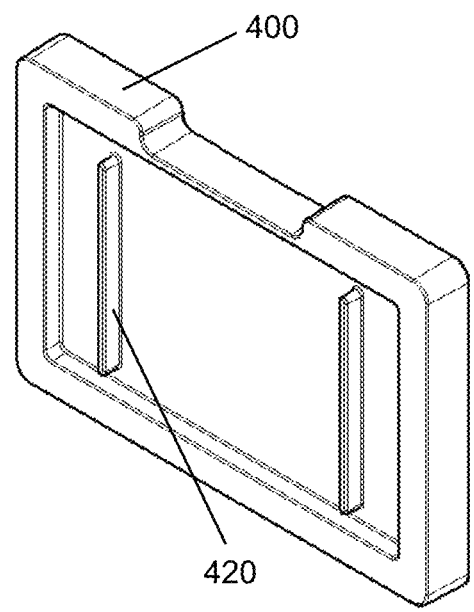
FIG. 7C illustrates the pusher accessory.
Figure 7D:
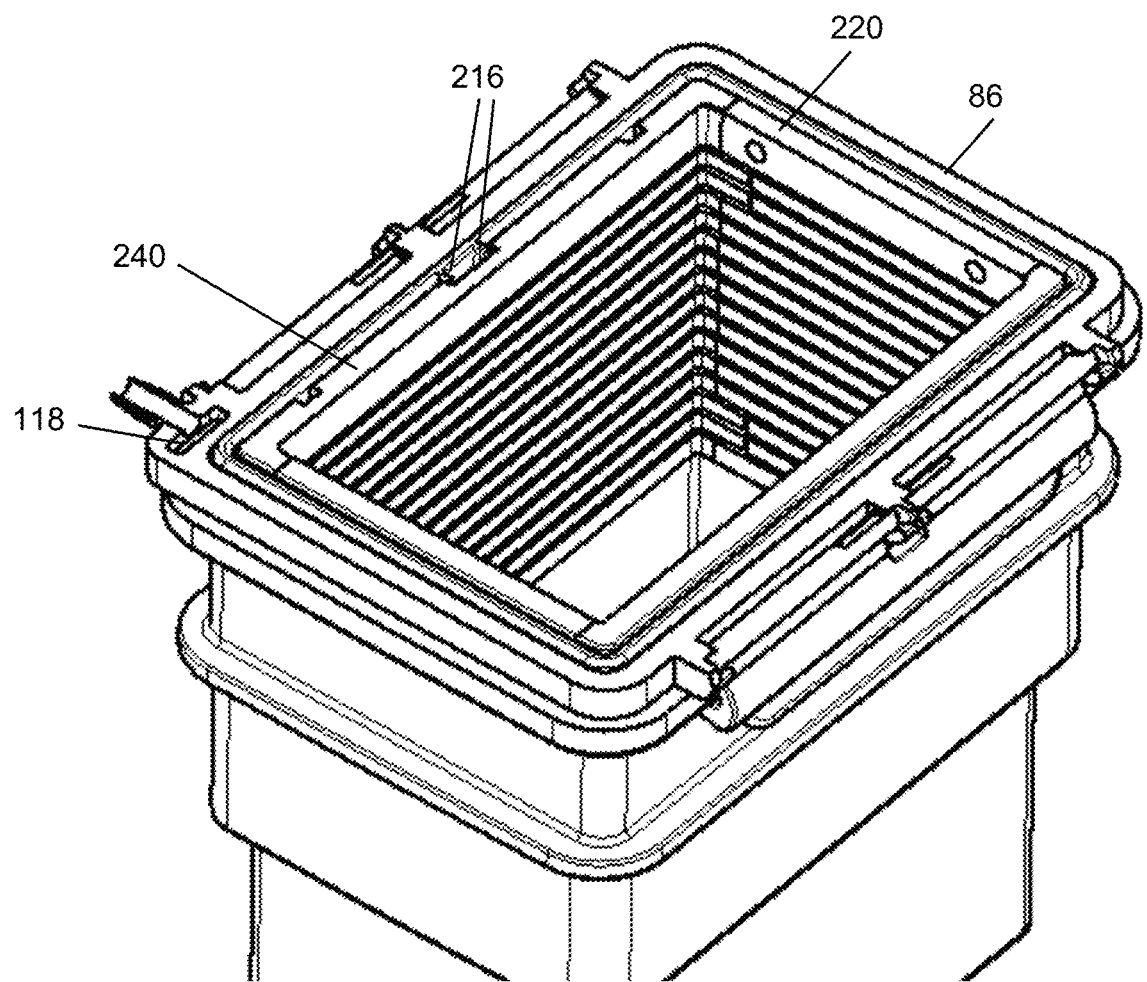
FIG. 7D illustrates a recess and boss for engagement of the screen holder with the upper manifold.
Figure 8:
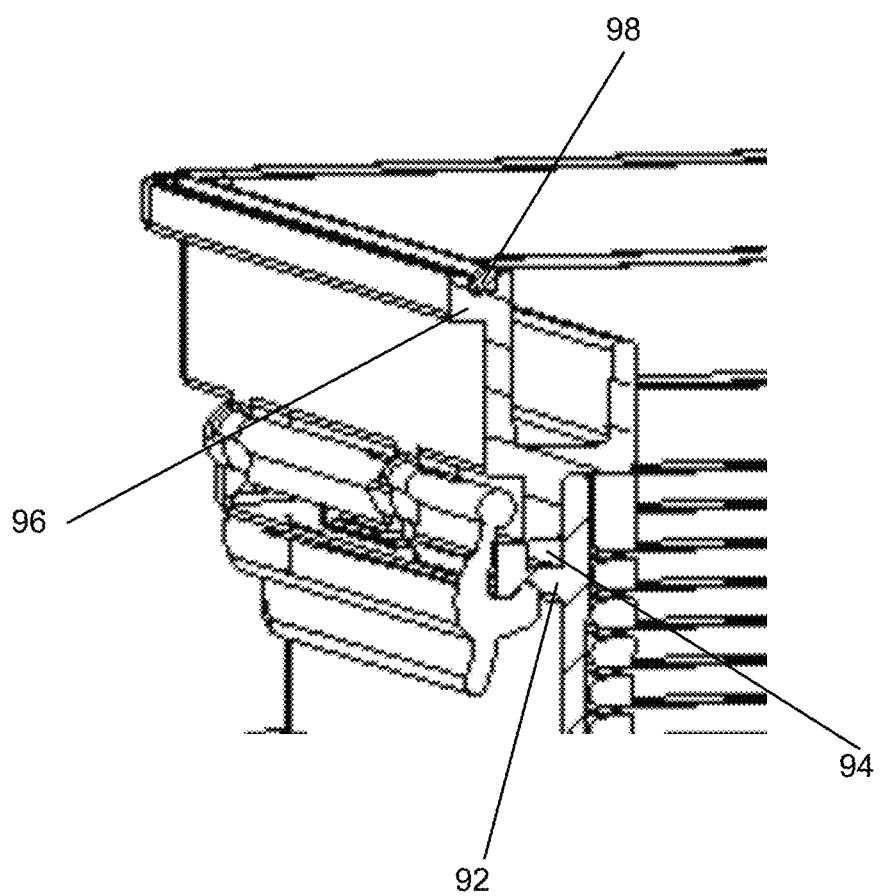
FIG. 8 illustrates details of seals.

In an embodiment of the invention, a start-up procedure can be as described here. At the start of use of the system, the reservoir container 60 can contain liquid medium up to a desired liquid level. The liquid level may be above the elevation of the bottom of lower manifold 82, and the amount of liquid contained may be sufficient for desired operations. Pump 140 may then be operated so as to withdraw fluid from moat 116. Pump 140 may be a positive displacement pump such as a peristaltic pump, capable of moving either liquid or gas or a combination thereof. Initially, pump will remove air from the region including upper manifold 86. This removal of air will cause the level of liquid medium to rise in lower manifold 82, into screen holder 300, and then upper manifold 86. Eventually the liquid level will reach the level of weir 112 and then begin to overflow weir 112 into moat 116. Liquid will then flow into sump 118. Pump 140 withdraws fluid from sump 118. It is possible that at some point during start-up, pump 140 will withdraw a mixture of liquid and gas from sump 118, but that is all right. Eventually there will be reached a steady state in which a substantially constant volume of gas remains in the region over upper manifold 86 and moat 116. As long as pump 140 continues to run, there will be a flowrate of liquid over weir (overflow wall) 112 into moat 116 and sump 118 and towards pump 140. It is believed that the level of liquid in moat 116 will be fairly close to the bottom of moat 116. This is illustrated in FIG. 6B. The liquid is indicated in FIG. 6B by the dotted-hatched pattern.

Pusher Accessory and Slots for Positioning of Screens

Referring now to FIG. 7, in embodiments of the invention, as described herein, the screen holder 200 may comprise positioning slots 390 that can be used for pushing screens 300 into a desired position or for defining positions of screens 300. Such positioning slots 390 may be generally vertical with respect to overall directions of the screen holder 200 and bioreactor 10. Positioning slots 390 may intersect other slots and grooves that are provided in screen holder 200.

A pusher 400 may also be provided as an accessory (for use before or after actual culturing). It is possible that the pusher 400 can be used on one side of the screen holder 200 for the purpose of pushing screens 300 into screen holder 200 until they contact a stop such as the base of groove 170. It is also possible that pusher 400 may be used on an opposite side of screen holder 200 for the purpose of pushing screens 300 out of screen holder 200, such as when culturing is completed or it is desired to remove screens 300. Positioning slots 390 on one side of screen holder 200 may have identical or similar dimensions and spacing as positioning slots 390 on another side of screen holder 200, which would enable a single pusher 400 to be used for pushing in both directions.

In order to facilitate the described pushing, pusher 400 may have certain dimensional relationships with appropriate features of screen holder 200. Bosses 420 on pusher 400 may be dimensioned, and may be spaced appropriately with respect to each other, so that they can fit into positioning slots 390 of screen holder 200. The height of the bosses 420 on pusher 400 may be sufficiently large so that the screens 300 may be pushed to a desired extent.

Features that Affect Engagement Between Screen Holder and Lower Manifold

It is further possible that there may be provided inter-engaging features that constrain or guide the inter-engagement between screen holder 200 and lower manifold 82. Such features may be referred to as a key and a keyway. As illustrated, screen holder 200 has a recess 210, and lower manifold 82 has a boss 216. Of course, the opposite is also possible, i.e., a boss on screen holder 200 and a recess on lower manifold 82. If screen holder 200 has some degree of symmetry, such as being of a rectangular cross-sectional shape, the key and keyway may limit the number of ways in which screen holder 200 and lower manifold 82 can be assembled together. This arrangement may serve to control the positioning of screens 300 when screen holder 200 is assembled with the rest of bioreactor 10.

There are some dimensional considerations in regard to insertion of screen holder 200 into lower manifold 82. For example, the width (in a horizontal direction) of boss 216 may be less than the width of recess 210.

If desired, the portions of the boss 216 or the recess 210, or both, that engage each other initially upon insertion of the screen holder 200 into lower manifold 82, may be provided with rounding features at one of their ends (at the top of the feature on the lower manifold 82, or at the bottom of the feature on the screen holder 200, or both), so as to guide the initial engagement between screen holder 200 and lower manifold 82. It is also possible that a rounded feature may be provided at other places at the bottom of screen holder 200, or at the top of lower manifold 82, or both, so as to guide the initial engagement between screen holder 200 and lower manifold 82.

Incubator

Figure 9:
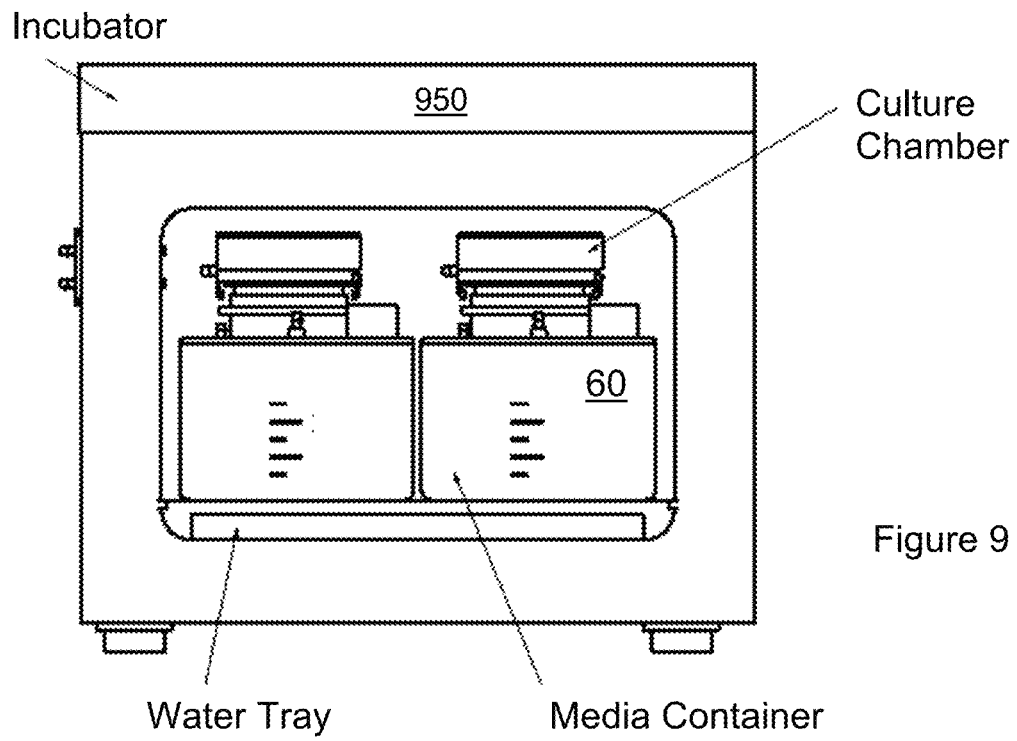
FIG. 9 illustrates placement of two bioreactors of embodiments of the invention within an incubator.

Referring now to FIG. 9, the bioreactor 10 may comprise an incubator 950. The incubator 950 may maintain within itself conditions that are conducive to cell growth. The incubator 950 may maintain a temperature that is a desired value that is close to physiological temperature. The incubator 950 may also maintain an atmosphere having a desired composition. The composition may have an oxygen concentration of approximately 20% and a carbon dioxide concentration of approximately 5%. The incubator 950 may also maintain a desired relative humidity of the atmosphere inside the incubator 950. The incubator 950 may have a front door providing access to the interior of the incubator 950 for installation or removal of major components. The incubator 950 also may have penetrations or pass-through through various of its walls. Such pass-through and penetrations are described here for a particular design, although it can be understood that other such arrangements are also possible.

At a location outside the incubator there may be a pump 140 for circulating or controlling the flow of liquid media. Pump 140 may be a positive displacement pump such as a peristaltic pump. There may be appropriate pass-throughs or penetrations for passage of such liquids into and out of the incubator 950 to and from the pump 140. Locating the pump 140 outside of the incubator may serve some specific purposes. One such purpose is that the electronics in the pump 140 may have a limit on the humidity to which they can be exposed, which may be lower than the relatively humid conditions that are usually maintained inside the incubator 950. Locating the pump 140 outside the incubator 950 eliminates this concern. Additionally, if the pump 140 was located inside the incubator 950, it could generate heat when it was running, and that heat could affect the control of temperature inside the incubator 950. Appropriate controls and, if desired, automation, may be provided for the pump and related systems.

The just-described parts may be suitable to be placed inside a controlled-environment chamber that may be referred to as an incubator 950. Incubator 950 may have controls to maintain within its interior a desired temperature, a desired atmospheric composition, a desired oxygen concentration, a desired carbon dioxide concentration, a desired humidity, desired values of any other environmental property, or any combination of these. The incubator 950 may have a door to permit the passage therethrough of these components, and the door may be closeable and sealable. The incubator 950 may further have passthroughs, through the incubator wall or boundary, which may be separate from the door. Such passthroughs may permit the passage of liquid into and out of the interior of incubator 950. The incubator 950 may further have connections through which oxygen or carbon dioxide may be supplied to the interior of incubator 950. Pump 140 for circulating liquid medium may be located external to the incubator 950. Passthroughs may provide for the passage of liquid medium into and out of the incubator 950. The incubator may be suitable to maintain sterility or at least cleanliness at and near the described components such as the assembly of manifolds 82, 86 and the reservoir container 60.

Connected to overflow moat 116 may be an exit fitting. The exit fitting may exit the moat such that at a portion of the interior open space of the fitting is at or below the level of the base of the moat 116. From exit fitting, there may be tubing or similar fluid-carrying means going to the intake of the pump 140. Tubing may be capable of conducting fluid (either liquid or gas) from the moat 116 to the pump. Pump 140 is shown as being located outside the incubator 1950. This pump location is optional, although advantages of it are discussed elsewhere herein.

Downstream of the pump 140, flow may proceed back into the incubator 950 and to a showerhead 186. The showerhead 186 may be located inside incubator 950 at the top of the reservoir container 60. The showerhead 186 may distribute the liquid medium in the form of drops that fall back into the reservoir container 60. The atmosphere inside the incubator 950 may have a desired concentration oxygen, and a desired concentration of carbon dioxide, and may also be temperature controlled. During the passage of drops of liquid medium from the showerhead 186 through the atmosphere inside the reservoir container 60, the liquid drops may exchange gas with the atmosphere inside the reservoir container 60, such as absorbing carbon dioxide from the atmosphere inside the reservoir container 60. The drops may also thermally equilibrate with the atmosphere inside the reservoir container 60 if needed. The drops may then collect in liquid region of reservoir container 60.

Flow of fluid through the entire described flow path may then be repeated.

Figure 10A:
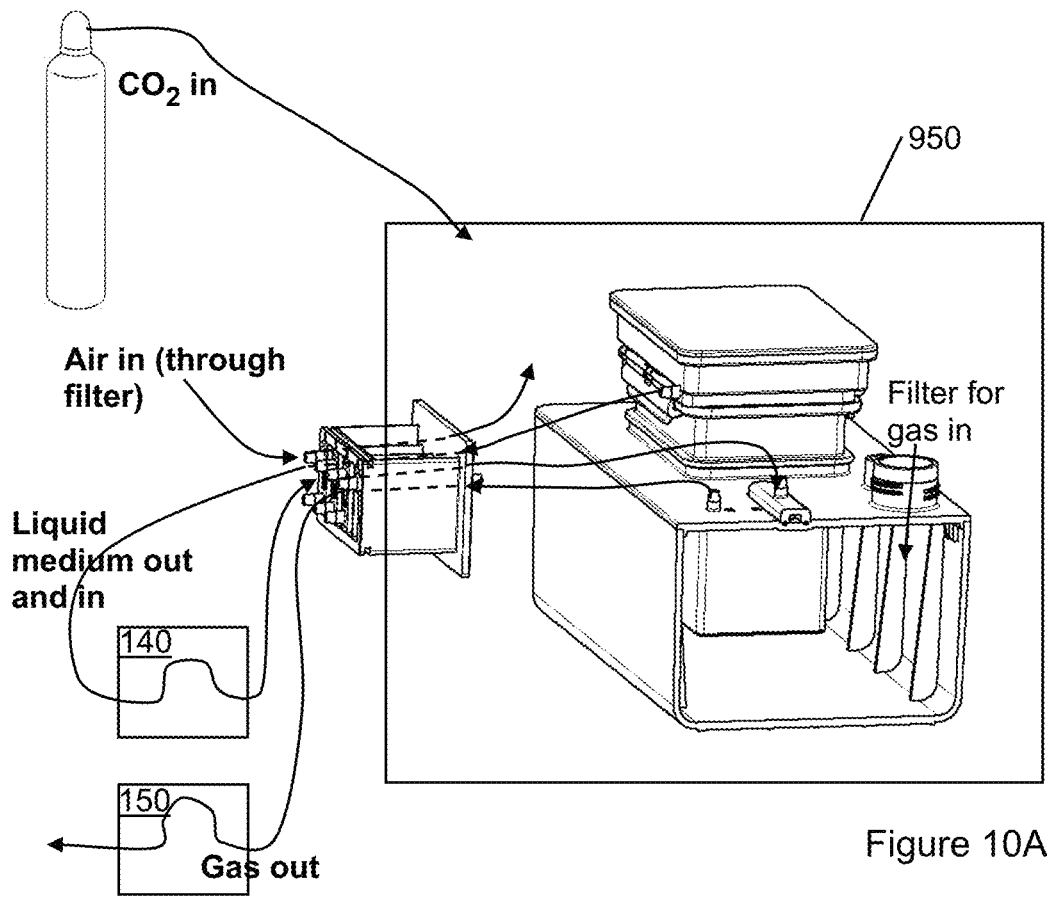
FIG. 10A illustrates flowpaths of various gases and liquids including into and out of the incubator and into and out of a reservoir container and manifold assembly.
Figure 10B:
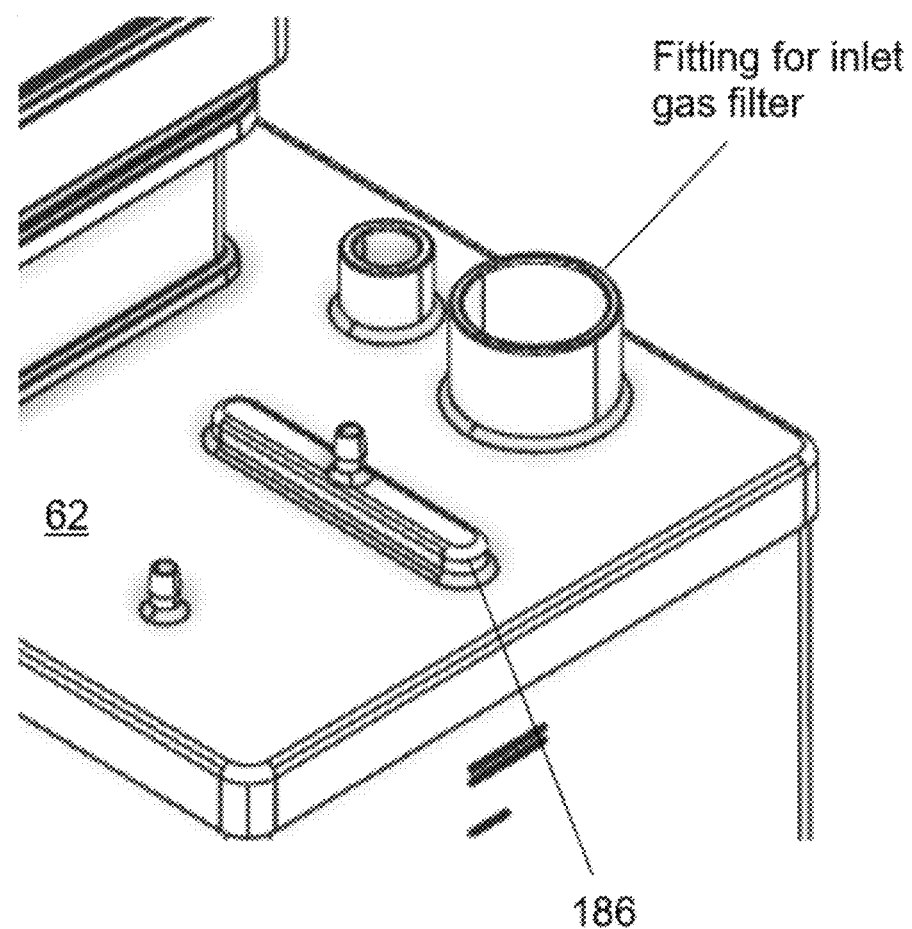
FIG. 10B illustrates a showerhead connected to the reservoir container.

Reference is now made to FIG. 10, which illustrates various connections through the boundary of the incubator 950 and the reservoir container 60. The bioreactor 10 may comprise connections for pump 140 to withdraw liquid medium and to re-introduce liquid medium. This provides dynamic circulation or perfusion of the liquid medium. If the pump 140 is located outside the incubator 950, the liquid medium can exit from the bioreactor 10, pass through the boundary of the incubator 950, pass through the pump 140, pass again through the boundary of the incubator 950, and re-enter bioreactor 10. More specifically, the liquid medium can exit from the sump 118 that is connected to moat 116, and can re-enter the reservoir container 60 through showerhead 186. The atmosphere inside the incubator 950 and the reservoir container 60 may be managed in several ways. CO2 may be supplied from a source outside the incubator 950 and, as illustrated, passes through a passthrough that is a permanent part of the incubator 950, shown as being on the rear of incubator 950. Air can pass from outside the incubator 950 into the interior of incubator 950 through a passthrough that is shown on the left side of incubator 950. This entering air may pass through a filter 960, which may be located outside the incubator 950. Thus, the atmosphere inside the incubator 950 may be a mixture of air and CO2. The gas space of reservoir container 60 may have an air extraction connection by which gas from the gas space of reservoir container 60 is pulled out of reservoir container 60, through a passthrough through the boundary of incubator 950, and out to an airflow pump 150. Airflow pump 150 may be a peristaltic pump, which may be located outside incubator 950. Gas from the atmosphere inside incubator 950 enters the reservoir container 60 through a filter (not illustrated) on port 940. Inside reservoir container 60, the showerhead 186 entrains some of that gas. The showerhead 186 causes aeration and exposes the liquid medium to CO2 and to oxygen. Cells obtain both CO2 and oxygen from the liquid medium for their metabolism and for the ATP cycle for energy transfer. The showerhead 186 as illustrated has nonuniform hole size distribution in order to form a spray with the desired characteristics and distribution. The liquid enters from above the showerhead 186 near the center of the array of holes. Holes that are more outwardly located are larger in dimension than holes near where the liquid enters.

As illustrated, two of the passthroughs through the left wall of the incubator 950 are for liquid medium to go into and out of the incubator. There is also a passthrough through the wall of the incubator by which an airflow pump, which may be a peristaltic pump, pulls atmosphere out from the gas space of the reservoir container 60. There is also a passthrough through which air from outside the incubator 950 enters the incubator interior, passing through a filter 960.

Embodiment Comprising a Rotor and Two Different Orientations of Flow

In general, there are at least two possible geometries of planar scaffolds and flow in bioreactors. The previously described embodiment involved flow through a screen generally perpendicular to the plane of the screen. Another possible geometry involves flow of liquid in a direction that is generally parallel to a screen. Each orientation has respective advantages and disadvantages.

Figure 11:
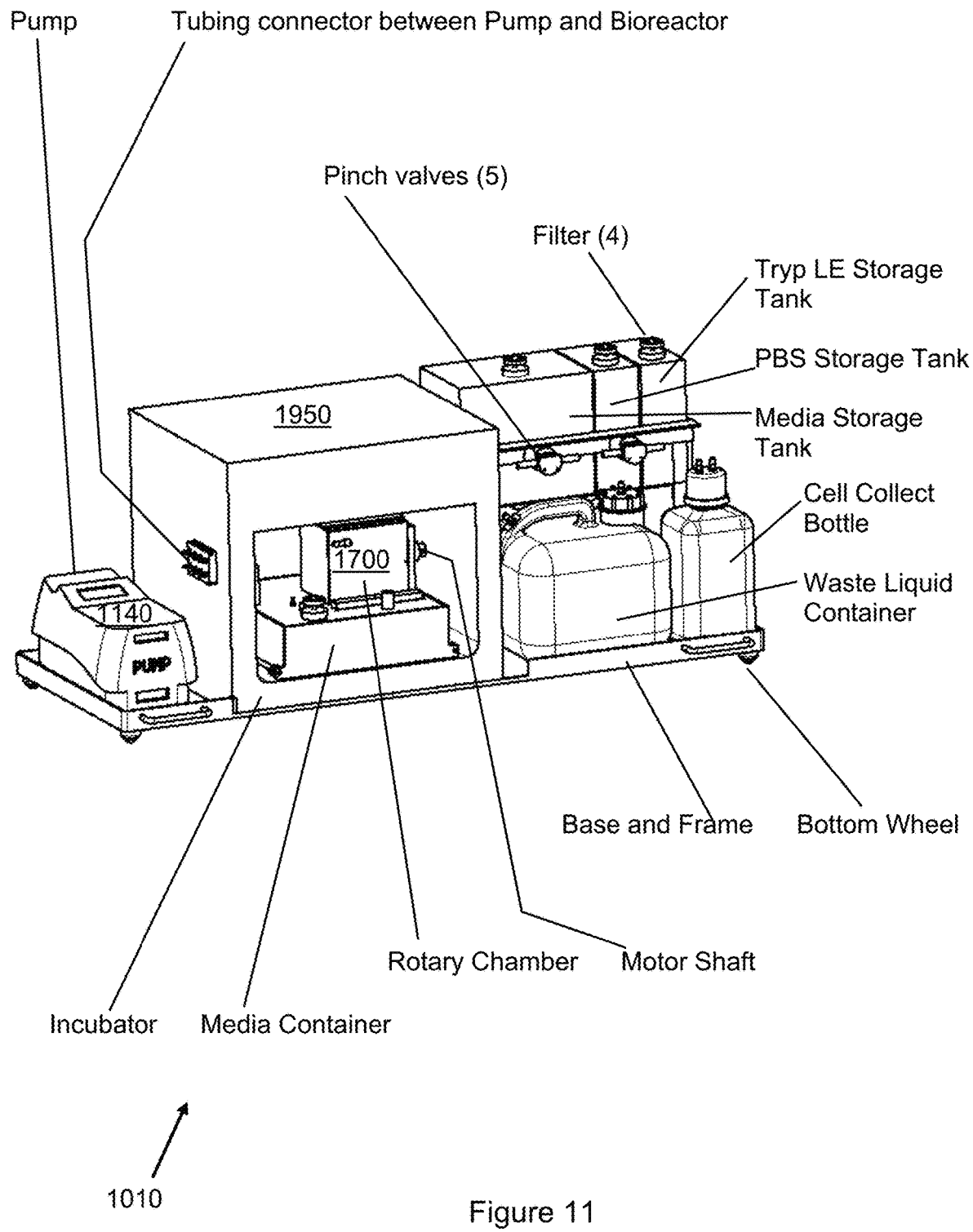
FIG. 11 shows an overall layout of a bioreactor of another embodiment of the invention.

In this next embodiment of the invention, a bioreactor 1010 may have overall components and an arrangement as illustrated in FIG. 11.

The described components may be attached to a base or frame that defines their locations and allows the apparatus to be carried as a unit. External to the apparatus there may also be provided a source of carbon dioxide, such as a pressurized tank. Similarly, a source of oxygen may be provided if desired.

Flow Path

Figure 12:
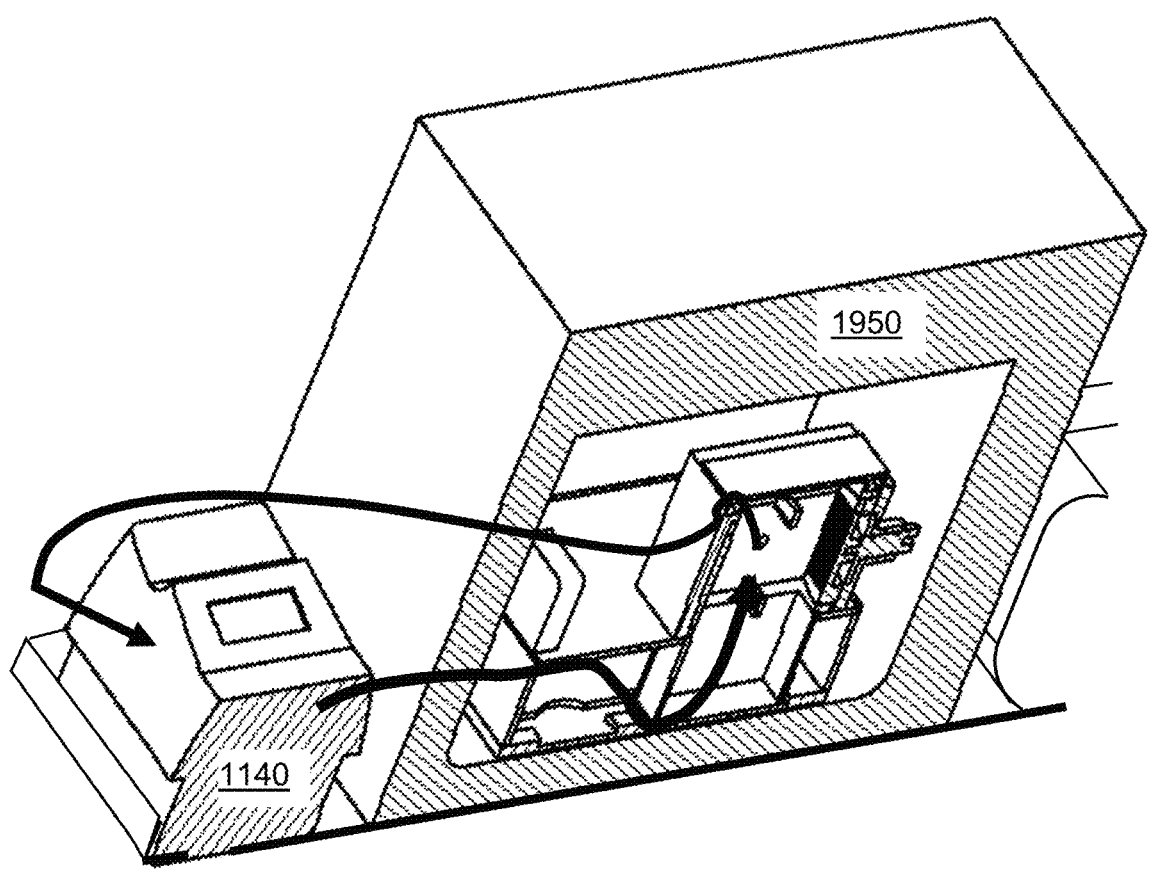
FIG. 12 shows an overall fluid flow path within the bioreactor.

Referring now to FIG. 12, for an embodiment of the invention, there is shown a fluid flow arrangement for the bioreactor 1010. As illustrated, the direction of liquid flow past the cell culture scaffold may be in a generally upward direction with respect to gravity. The flow can flow in a recirculating flow path. In an embodiment of the invention the liquid medium is able to flow in a recirculation path from a reservoir, upward through the scaffold, through a pump, through a showerhead, and back to the reservoir.

The pump 1140 may be capable of self-priming by pumping gas through the pump initially so as to pull liquid up from the lower reservoir into the cell culture region. Thereafter, the pump 1140 may be able to move liquid when it is desired and at whatever rate it is desired to circulate liquid through the culture region. The pump 1140 may be a positive displacement pump such as a peristaltic pump.

The apparatus may comprise a reservoir container 1060, which may be located generally at an elevation that is lower than the elevation of various other components of the apparatus. The bottom of the reservoir container 1060 may be formed, at least in part, by a reservoir base 1400 that is generally flat and horizontal having a reservoir base upper surface 1410. The reservoir 1060 may further be defined by reservoir sidewalls and a reservoir lid. Furthermore, reservoir base 1400 may have some features that are recessed below reservoir base upper surface 1410.

The reservoir 1060 may have therewithin a stirrer such as a magnetic stirrer bar (not illustrated) that can be caused to rotate by an externally applied magnetic field that rotates. The stirrer bar may be more dense than the density of the liquid so that the stirrer bar may sink due to gravity and rest upon a surface of the reservoir base, more particularly a bottom surface of stirrer recess 1420. Alternative stirrer arrangements are also possible, such as a rotating rod and paddle.

The stirrer bar could be rotated at an appropriate rotational speed to maintain cells in suspension in the liquid so that the liquid drawn into the scaffold contains appropriate cells.

Reservoir Base

Figure 13:
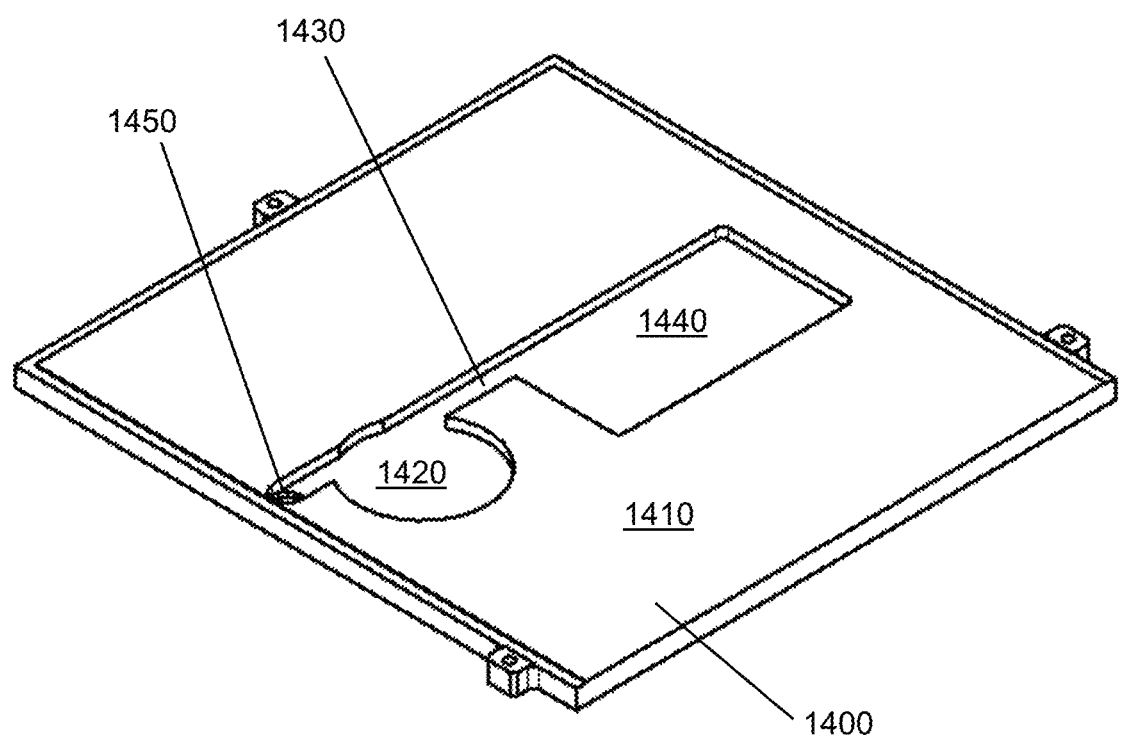
FIG. 13 shows a reservoir base including several recesses.
Figure 14:
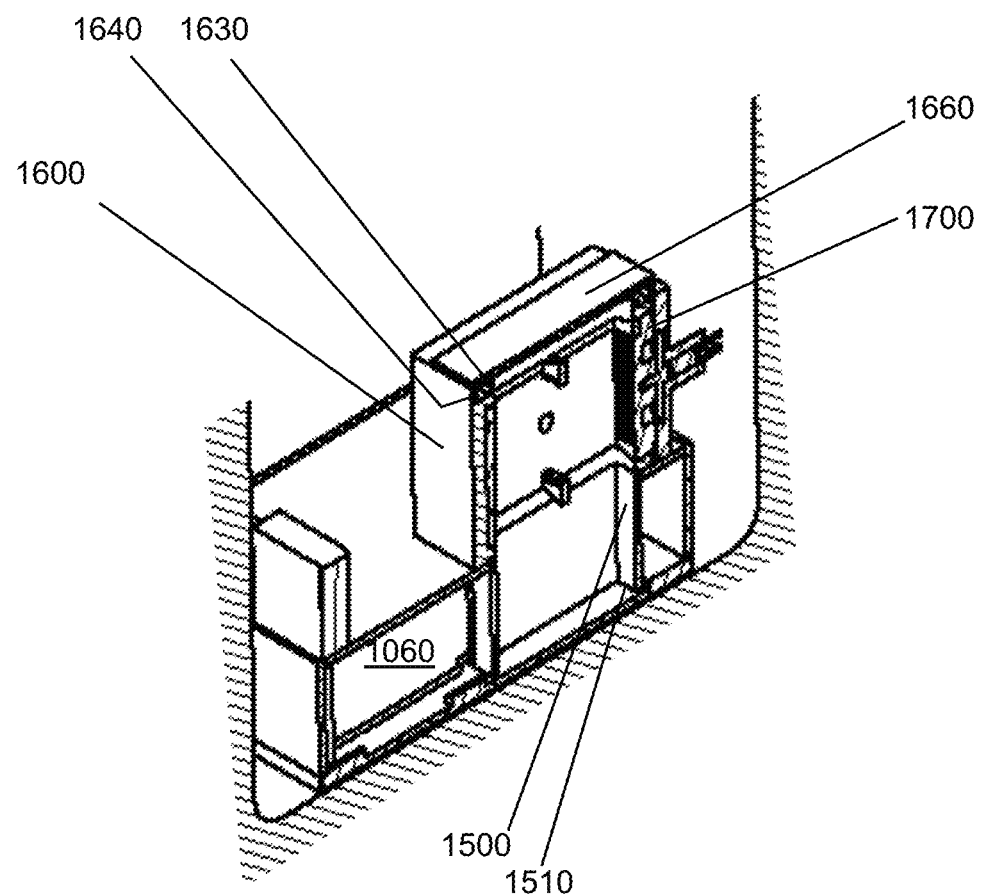
FIG. 14 shows the riser conduit and nearby components.
Figure 15:
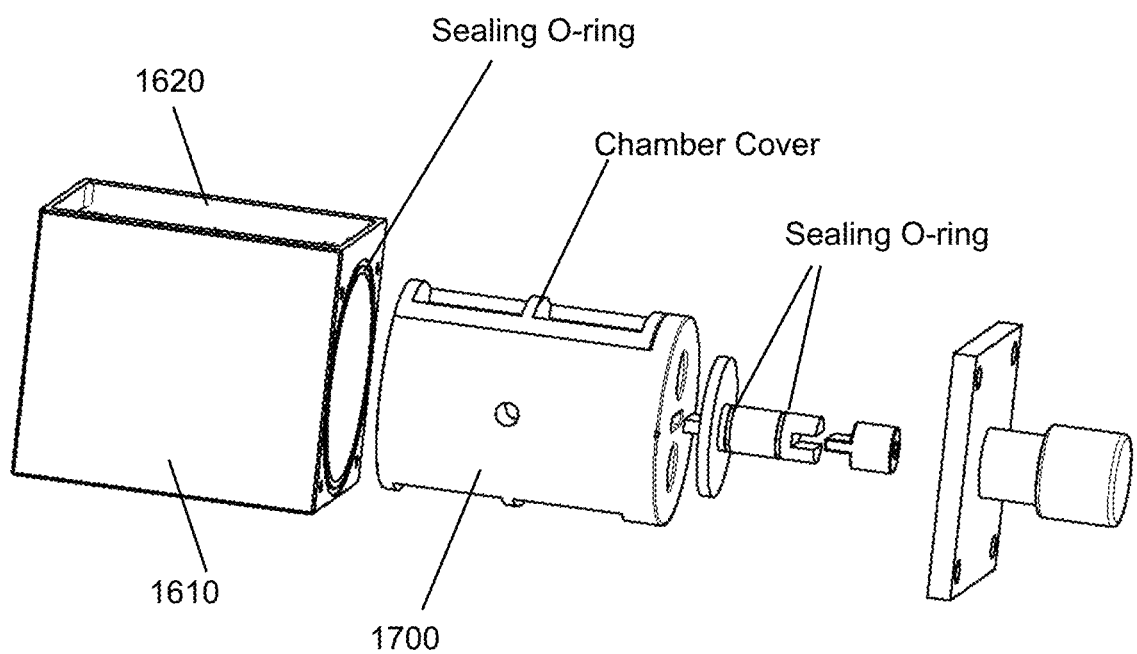
FIG. 15 shows an exploded view of the rotor chamber and rotor.

The reservoir 1060 may be defined in part by reservoir base 1400. Referring ow to FIG. 13. reservoir base 400 may be generally flat and horizontal but may have a pattern of recesses recessed into it.

Corresponding to the stirrer bar, there may be a stirrer recess 1420, recessed into reservoir base 1400. Stirrer recess 1420 may be, in its horizontal dimensions, larger than the path that is swept out by the stirrer bar. At least some of the stirrer recess 1420 may be approximately cylindrical and may have a bottom that is flat and horizontal. The depth of the stirrer recess 1420 can be less than the vertical dimension of the stirrer bar, if desired.

There may further be provided a canal recess 1430 that may be generally straight in a lengthwise direction. There may further be provided a reservoir sump recess 1440. The canal recess 1430 may intersect with the stirrer recess 1420, and may intersect with the reservoir sump recess 1440.

The floor surfaces of all of these recesses (stirrer recess 1420, canal recess 1430, reservoir sump recess 1440) may be planar and may be coplanar with each other and may be generally horizontal. Places where the various recesses (stirrer recess 1420, canal recess 1430, reservoir sump recess 1440) intersect each other may be provided with rounded corners to improve the smoothness of fluid flow. At various places associated with the recesses, there may also be provided internal corners that are rounded.

There may also be provided a drain recess 1450 that may be in fluid communication with the canal recess 1430 and may extend to a lower elevation than does the canal recess 1430. Fluid can be removed from the reservoir 1060 by putting a tube into the drain recess 1450 from above and suctioning fluid out.

Referring now to FIGS. 14-16C, there may also be provided a riser conduit 500 that may define a flow path leaving the reservoir 1060 in an upward direction. The riser conduit 1500 is illustrated as being of rectangular cross-section, but it can be appreciated that other cross-sectional shapes are also possible. The riser conduit 1500 may have a riser conduit lower edge 1510 that is flat and horizontal. First of all, the riser conduit 1500 may be positioned such that the riser conduit lower edge 1510 is at a lower elevation than the elevation of the liquid level in the reservoir 1060. More particularly, the riser conduit 1500 may be positioned so that the riser conduit lower edge 1510 is located at an elevation that is higher than the floor of the reservoir sump recess 1440, but is lower than the upper surface 1410 of reservoir base 1400. It may also be provided that reservoir sump recess 1440 has a boundary that is larger than and outside the outer perimeter of riser conduit 1500. This combination of dimensional relationships may provide an inflow pattern, for flow from the reservoir 1060 into riser conduit, that is distributed generally around the entire perimeter of riser conduit 1500. Such a flow pattern preserves access to a very large fraction of the liquid in the reservoir 1060, while not creating "pinch points" that have excessively high local fluid velocities or local shear rates in the fluid flow.

Continuing upward along the general direction of riser conduit 1500, there may be rotor chamber 1600 and rotor 1700 that is contained generally within rotor chamber 1600. More detail about rotor 1700 is provided elsewhere herein.

Rotor chamber 1600 may have therethrough a vertical passageway defined by the lower pass-through opening 1610 and the upper pass-through opening 1620. Lower pass-through opening 1610 and upper pass-through opening 1620 may have substantially identical internal cross-sectional area and dimensions. The internal cross-sectional area and dimensions of lower pass-through opening 1610 and upper pass-through opening 1620 may at least approximately match those of the interior of riser conduit 1500 and those of the passageway (described elsewhere herein) through the rotor 1700.

Rotor chamber 1600 may rest upon or may be mounted upon the cover plate of reservoir 1060.

Near the top of rotor chamber 1600 the rotor chamber wall that touches the liquid may end at a top edge 1630 that is flat and horizontal. The top edge 1630 may act as a weir for liquid to flow over it. Outside of the wall may be an overflow moat 1640. The design of the overflow moat 1640 and nearby features may be such that the fluid in the rotor chamber 1640 has to flow upward, then over the top edge 1630 of the rotor chamber wall, then downward into the moat 1640. The moat 1640 may extend around the entire perimeter of the rotor chamber 1600. During operation of the system, a gas pocket may be present above the top edge 1630.

Rotor chamber 1600 may be topped off by rotor chamber lid 1660, which may be removable. There may be a gap between the top edge 1630 and the rotor chamber lid 660. The gap may be suitable for flow to flow through the gap and thereupon the flow may enter and be collected by overflow moat 1640. It is believed, although it is not wished to be limited to this explanation, that the use of overflow moat 1640 may help to improve the uniformity of flow through the cell culture region and tissue scaffold. There may be an overflow moat 1640, and a corresponding sump, and showerhead as in another embodiment herein.

Rotor and Cell Culture Scaffold

Within rotor chamber 1600 there may be provided rotor 1700. Rotor 1700 may be able to rotate, with respect to rotor chamber 1600, around an axis of rotation. The axis of rotation may be horizontal, and may be generally perpendicular to the direction of the riser conduit 1500. Rotor 1700 may be close-fitting within rotor chamber 600, while still being free to rotate.

One end of the rotor 1700 may have or may have attached thereto a shaft to direct the angular position of the rotor 1700. The shaft may in turn be operated by a motor. The motor may be located inside the incubator 1950, or may be located outside the incubator 1950 with a penetration for the shaft to pass through the wall of the incubator 1950. The motor may be controlled by a computer or automation system.

The rotor 1700 may be able to rotate through various rotation positions. One position of the rotor may correspond to a full-open flow path for flow through the rotor interior and the tissue scaffold. Another position of the rotor 1700 may be such that the flow path is blocked by the generally solid portion of the rotor 1700.

With continued reference to FIGS. 14-16C, there is shown the rotor 1700 and some associated parts. The rotor 1700 may be generally cylindrical except for the absence of material as described herein. The rotor may have two opposed rotor openings 1710, 1712 defining a passageway through the rotor 1700, and the rotor may have two remaining opposed sides 1714, 1716 that are mostly-solid. Proceeding around the perimeter of the rotor 1700, there may be open space; a generally solid portion that may be cylindrical on its exterior; open space; and another generally solid portion that may be cylindrical on its exterior. On the exterior, the generally cylindrical shape may correspond to the internal cylindrical space within rotor chamber 1600. The dimensions of the mostly-solid sides may be such as to completely block the riser conduit 1500 (except for holes 1790) when the rotor 1700 is at an appropriate angular position. Rotor ends may have internally facing grooves 1720. The grooves 1720 in the rotor 1700 may be dimensioned appropriately to receive and support the edges of scaffolds or screens.

One of the rotor openings 1710 may have a bridge 1740 that spans the rotor opening. The other of the rotor openings 1712 may have a removable clip 1760 that spans the rotor opening. The bridge 1740 and the clip 1760 may be dimensioned so that they occupy only a small portion of the overall length of the rotor 1700 so as not to create a substantial disturbance in the flow of liquid. The bridge 1740 and the clip 1760 may have internal grooves that correspond to the internal grooves 1720 at the ends of the rotor 1700. In combination, the grooves at one end of the rotor 1700, the grooves at the other end of the rotor 1700, the grooves in the bridge 1740 and the grooves in the clip 1760 may all align with each other and may cooperate with each other to support the screens.

Within the open space in rotor 1700 there may be provided cell growth scaffold such as screens 1300 as is described elsewhere herein, and flow may flow past or through the cell growth scaffold such as screens 1300.

In the solid part of rotor 1700 that has the generally cylindrical exterior, there may be provided a hole 1790 or a plurality of holes 1790 therethrough on each of two opposed sides. The holes 1790 may align with each other. The holes 1790 may allow mass transfer between the liquid in the scaffold region interior of the rotor 1700 and the liquid in the reservoir during the time when the scaffolds are in a horizontal orientation. Even though when the scaffolds (screens) are horizontal there might be no bulk flow of liquid, holes 1790 would still allow some mass transfer even if it is only by diffusion or some form of natural convection.

The open space through the rotor 1700 may roughly correspond, in dimensions and cross-sectional area, to the internal dimensions and cross-sectional area of the riser conduit 1500. For example, the dimension from the inside of one of the generally solid portions of the rotor 1700 to the other of the generally solid portions of the rotor 1700 may be the same or approximately the same as the inside dimension, in the same direction, of the riser conduit 1500. The end-to-end dimension of the empty space of the rotor may be the same or approximately the same as the inside dimension in the same direction, of the riser conduit 1500.

The open space through the rotor 1700 may be the space intended to be occupied by an array of cell culture scaffolds 1300. Ends of the rotor 1700 that face internally to the open space may comprise grooves 1720 or similar interfaces to hold a plurality of cell culture scaffolds. As illustrated, the ends of the rotor 1700 each have grooves 1720 for 10 individual screens 1300. An alternative design could have grooves for some other number of screens 1300 as might be desired. The grooves 1720 can support or guide or position the ends of the screens 1300 at the edges of the screens 1300. The grooves 1720 may be dimensioned appropriately for the thickness of each scaffold or screen 1300, and for the intended spacing between the scaffolds or screens 1300. At an additional location such as midway between the two ends of the rotor 1700, there may be provided small auxiliary supports that also contain grooves 1720 to support or guide or position the screens or scaffolds 1300 at their edges. For example, there may be provided bridge 1740, which may be connected to the rotor 1700, which may contain grooves 1720. There may be provided a removable clip 1760 that is attachable to and detachable from rotor 1700, and which also may contain grooves 1720.

Design of scaffolds and screens could be as discussed elsewhere herein in connection with another embodiment.

As illustrated, the rotor 1700 contains grooves 1720 appropriate to hold the scaffolds 1300 for flow in a direction that is parallel to the surfaces of the scaffolds 1300. Alternatively, it would be possible to provide a rotor 1700 that holds the scaffolds 1300 in a position for flow through the scaffolds (perpendicular to the face of the scaffolds). The apparatus could be designed to be able to accept various different rotors 1700, with different rotors 1700 having different designs as far as placement or orientation of the scaffolds 1300. It is possible that with different interchangeable rotors, one rotor could provide flow generally parallel to the surface of the scaffolds while another different rotor could provide flow through the scaffolds, i.e., generally perpendicular to the scaffolds.

Considerations Related to Volume and Efficient Use of Cells and Media

Figure 17:
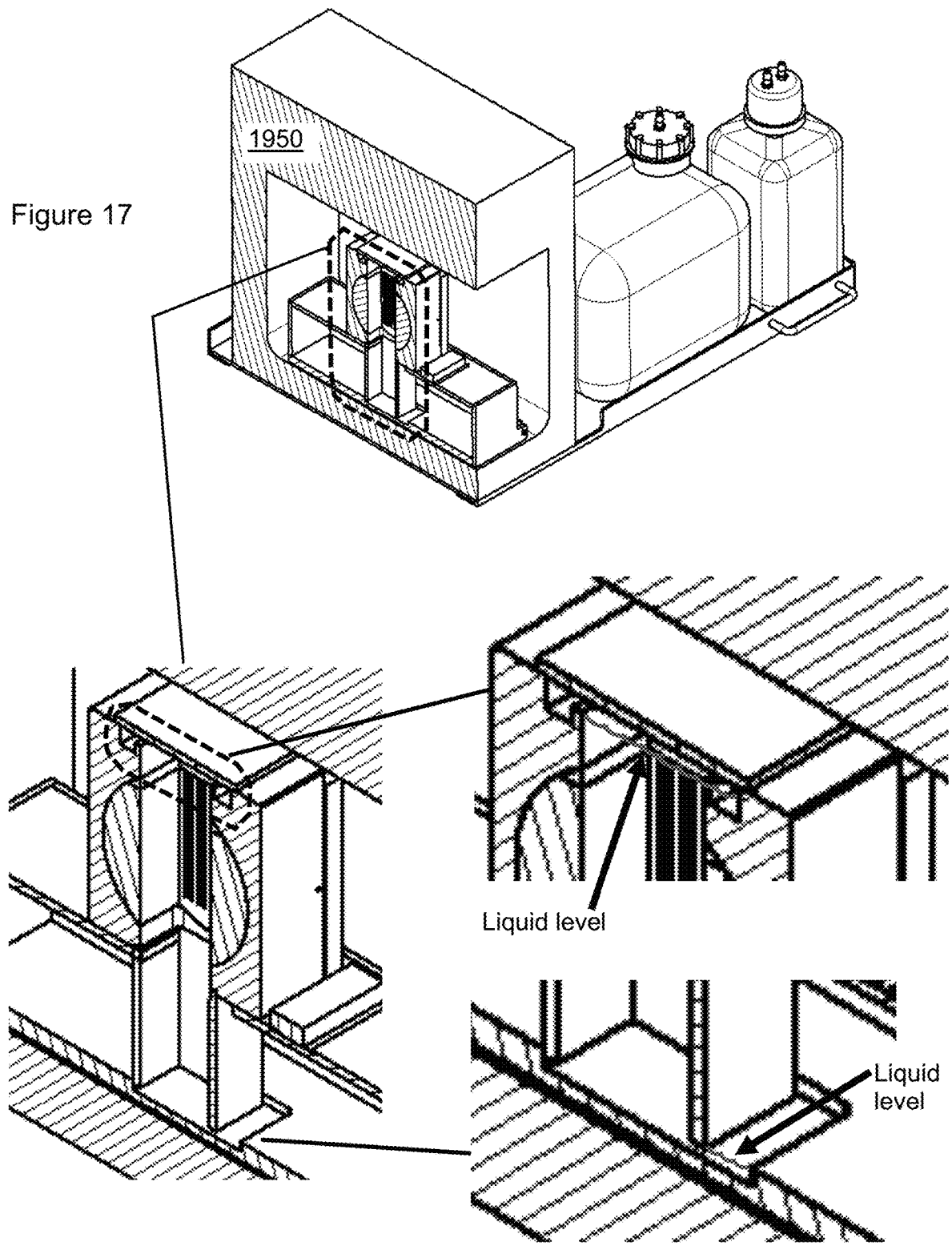
FIG. 17 shows details pertaining to the levels of surfaces of liquids in the bioreactor.

Referring now to FIG. 17, various considerations may be built into the design and operation of the apparatus to contribute to the efficient use of the medium, which can be an expensive material, and to the efficient use of cells, which tend to sink under the influence of gravity. The lower edge 1510 of riser conduit 1500 may extend submerged beneath the surface of the liquid in the reservoir 1060, or specifically may extend submerged beneath the surface of liquid in reservoir sump recess 1440, both prior to operation and also at all times during operation. This may contribute to the ability to suction fluid upward. In order to be able to suction liquid upward into the riser conduit 1500, it is preferable to avoid having any air travel under the lower edge 1510 of the riser conduit 1500.

The available volume of the reservoir 1060 may be defined as the volume of liquid present in the reservoir 1060, consistent with the requirement that the liquid level is lower than the showerhead and lower than the stopper in the fill port, and with the liquid level in the riser conduit being the same as the liquid level in the reservoir 1060 outside the riser conduit 1500 when the apparatus is equilibrated and not operating. The available volume of the reservoir 1060 may be sufficient so that when the reservoir 1060 contains an appropriate amount of liquid that is less than the available geometric volume of reservoir 1060, even when the rotor chamber 1600, the moat 1640, and various tubing are full of liquid, the reservoir 1060 is still not empty or at least reservoir sump recess 1440 is not empty. More specifically, at these conditions, the liquid level in the reservoir 1060 or reservoir sump recess 1440 is still at a higher elevation than the lower edge 1510 of riser conduit 1500.

The volume of the reservoir 1060 may be sufficient to fill all of these just-described spaces with liquid in the absence of screens being present in the rotor 1700. Alternatively, the volumes of various components may be calculated, and may be corrected for the amount of space occupied by the screens of the cell culture scaffold, and the volume of the reservoir may be sufficient to fill all of these just-described spaces when scaffolds are present. The volume of liquid that is actually loaded into reservoir 1060 may be measured out sufficiently accurately so that when the empty spaces such as riser conduit 1500, rotor chamber 1600, moat 1640 and various tubing are full of liquid, sufficient to reach the top of wall 1630 or at least to cover the scaffolds with liquid, the liquid level in reservoir 1060 may be in the reservoir sump recess 1440 but higher than the lower end of 1510 of riser conduit 1500.

It has been illustrated that the upper surface 1410 of reservoir base 1400 is flat and horizontal. Alternatively, it is possible that some slight slope or funnel shape could be provided to help drain liquid or to help liquid reach the reservoir sump recess 1440.

It can be noted that the pump 1140, such as a peristaltic pump, is downstream of the cell culture chamber, i.e., rotor chamber 1600. This means that during seeding of the scaffold, cells can reach the scaffold directly from reservoir 1060 without having to pass through the pump. Passage of cells through the pump could conceivably damage the cells undesirably. However, it is anticipated that during seeding, most of the cells that occupy the region of the cell scaffold will deposit themselves on the scaffold. It is anticipated that only a small fraction of the cells will fail to seed and will exit the rotor chamber 1600 and pass through the pump 1140. If, upon passage through the pump 1140, there is damage to those cells that failed to attach to the scaffold, those cells should be few in number anyway, so possible damage to those unattached cells should not have much overall significance in terms of the efficiency of using cells.

It is possible that the direction of rotation of the stirrer bar can be such that it urges flow of liquid that is in canal recess 1430 toward riser conduit 1500. As such, it would thereby provide some amount of useful pump-like action, especially when the liquid level in reservoir 1060 is low, in addition to stirring action.

Filler Structure Inside Riser

Figure 18:
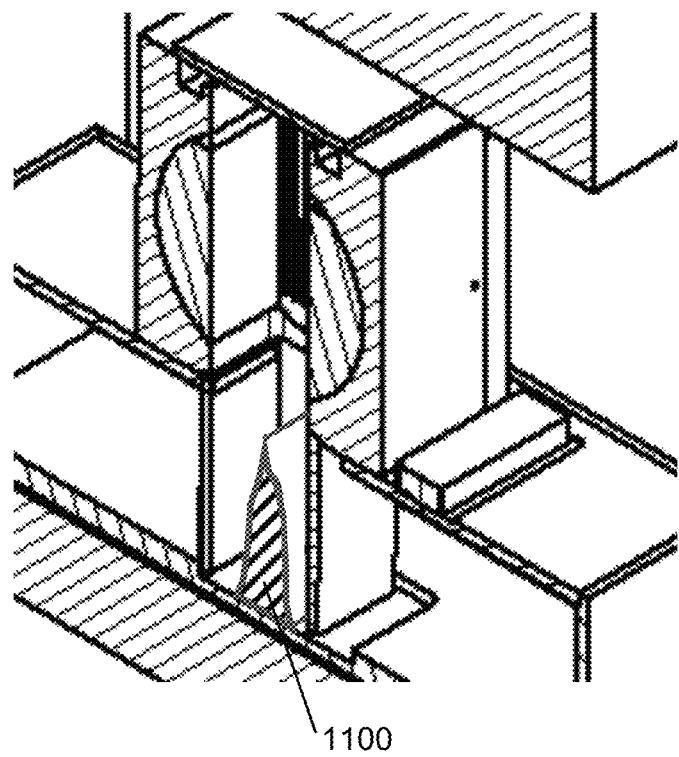
FIG. 18 shows a filler structure inside the riser conduit.
Figure 18:
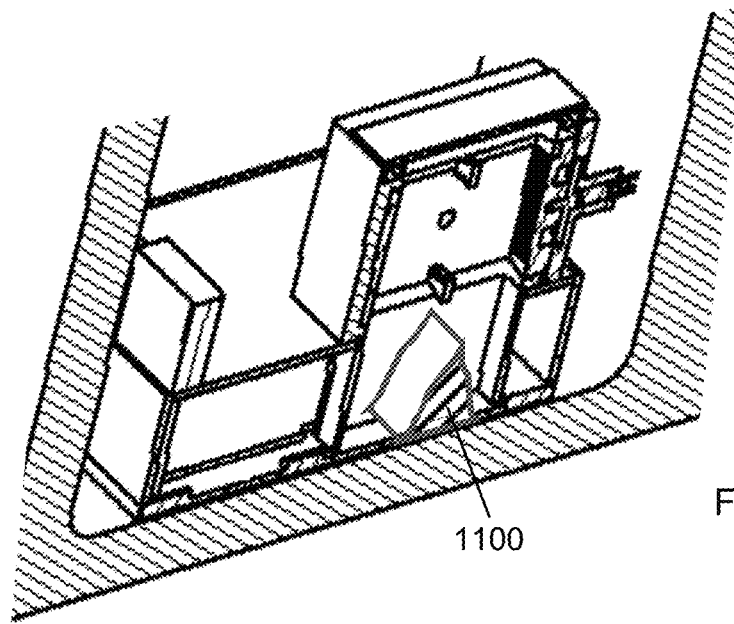

Referring now to FIG. 18, in an embodiment of the invention, there may be provided a filler structure 1100 inside the riser conduit 1500.

The filler structure 1100 may usefully occupy some portion of the volume inside riser conduit 1500 so that that portion of the volume does not have to be occupied by media liquid. Because media liquid is expensive, and liquid media that is in the riser is does not contribute to cell seeding or culture, the filler structure 1100 may reduce such amount of media that does not serve a useful purpose.

The filler structure 1100 may have a streamlined shape so as to receive flow of media that enters at the bottom of the riser at the riser sump, and direct and distribute that flow upward toward the cell culture region. Accordingly, the upper end of the filler structure 1100 may be pointed, pointing vertically upward. The lower end of the filler structure 1100 may be such as to receive flow that has a horizontal component of velocity coming from the reservoir sump recess 1440, and redirect that flow upwardly.

It is also possible to use a filler structure resembling filler structure 1100 in other embodiments of the invention. Even if this is not done for the purpose of conserving the amount of liquid medium, it could be beneficial for improving the flow patterns, such as improving the uniformity of velocity distribution, of flow entering the array of screens.

At a location outside the incubator 1950 may be a plurality of fluid containers. Such fluid containers may include a waste liquid bottle; a retrieval bottle; a media storage bottle; a PBS (phosphate buffered saline) bottle; and a tryp-LE E bottle. There may be appropriate pass-throughs or penetrations for passage of such liquids into and out of the incubator 950. Appropriate valves may also be provided for controlling the flow of such liquids. At this location, or generally at whatever location is desired, there may also be provided a motor capable of rotating a cell culture component such as a rotor, as is described elsewhere herein.

Impactor

In embodiments of the invention, there may also be provided an actuator or impactor (not illustrated) that may be suitable to direct motion at or deliver an impact to the apparatus inside the incubator 1950, such as the exterior of the rotor chamber. The vibration caused by the impactor striking a component near the cell culture screens may dislodge cells and may help in harvesting the cells after expansion. In the illustrated embodiment, the impactor could be located at the rear of the incubator 1950. There may be an appropriate pass-through or penetration for the impactor. This impacting may be done in conjunction with a chemical treatment such as exposing the cell population to trypsin.

The apparatus may also comprise automatic controls appropriate to operate the described components.

Methods of Operation

In embodiments of the invention, seeding and growth of the cells onto the scaffold may be performed by various protocols.

During seeding, the liquid in the reservoir 1060 could contain cells to be seeded. During cell expansion, the liquid in the reservoir 1060 does not need to contain cells, but it could contain nutrients that are conducive to the growth and multiplication of cells.

It is contemplated that during the seeding stage, the cells/media mixture will essentially not go through the pump 1140. At the start of the automatic seeding process, the cells and media are in the reservoir 1060. The media volume at this time could be enough to fill the riser and the cell culture region, but not much more than that. When the pump 1140 starts, this cells/media mixture will be suctioned up into the cell culture region. It is only necessary to suction up enough media to cover the cell culture scaffold (screens) with liquid. It is unnecessary to fill the moat 1640 with liquid, and it is unnecessary to suction liquid far enough for liquid to enter into the tubes that go from the moat 1640 to the pump 1140. This operation can be performed such that when the rotor chamber 1600 is filled with cells/media mixture, the pump 1140 will stop. For example, with a peristaltic pump, if the rotor of the peristaltic pump stops rotating, there will be no further flow and there will be no backflow. So, the pump 1140 can simply be shut off and the liquid can be allowed to remain where it is at that time, including the liquid level in the culture region. It is possible that the volumes of liquid may have been calculated and measured sufficiently accurately so that at that point the reservoir 1060 is nearly empty. In fact, it is possible that the liquid level in the reservoir 1060 may have dropped to somewhere in the reservoir sump recess 1440. If the liquid level is in the reservoir sump recess 1440, lower than the upper surface 40 of reservoir base 1400 but higher than the bottom end of riser conduit 1500, the liquid inside the riser conduit 1 500 and the cell culture region will be maintained in a stable position because there will be no passage of air bubbles into the liquid column to allow liquid to fall. The cell/media will be maintained inside the riser column 1500 and the cell culture region by the reduced gas pressure (which may be slightly sub-atmospheric) above the cell culture region, even though the pump 1140 is stopped at that time. A pump such as a peristaltic pump, or generally a positive-displacement pump, may maintain such a situation. Valving could also be used.

In the process of seeding, media containing cells may be raised by suction into the region of the rotor 1700 and the cell culture scaffolds. For initial inflow of liquid, the position of the screens 1300 may be generally vertical. The seeding process can then start by rotating the rotor 1700 so that the screens 1300 occupy a horizontal position. This allows cells that are suspended in the liquid between the screens 1300 to settle downward by gravity onto the adjacent screens 1300. The scaffold (screen) 1300 may be maintained in a stationary condition for a period of time as this happens. It is also possible that at desired times, the rotor 1700 can again be rotated. For example, the rotor 1700 might be rotated 180 degrees so that cells that might be merely resting unattached on top of one screen 1300 might float away and settle on and attach to a nearby screen 1300 due to the change of the gravitational direction. The rotor 1700 can be rotated periodically to produce a uniform cell distribution on the screens or scaffold. This process may continue for as long as one to two days (to be determined by experiment).

When seeding is completed, it is expected that all (or most) of the cells will be attached to the scaffolds (screens) 1300. The follow-up steps may involve a more continuous flow of culture medium and can be termed dynamic culturing. Additional media can be added to the reservoir 1060. This additional medium does not need to contain cells. The pump 1140 may be turned on to allow dynamic culture by means of media circulation. The flow can flow continuously around the flow system through the scaffold, if desired. The flowrate can be adjusted to be low enough to keep the shear rate at the cell locations to a desirably small magnitude. At this point, there may be some cells that have not attached to the scaffolds and that flow through the pump tubing. It is hoped to achieve at least 80% seeding efficiency in the seeding process.

The procedure as far as operation of the motor and positioning of the scaffold screens could be as follows:
[0163] Fill the reservoir 1060 with liquid that contains cells to be cultured and expanded. [0164] For initial filling of the culture region with liquid, position the screens vertically. [0165] After the initial filling of the culture region with liquid, position the screens (scaffold) 1300 horizontally so that cells that are in suspension between the screens can settle out of suspension onto the screens. [0166] At intervals, rotate the screens 180 degrees so that upward-facing screen surfaces become downward-facing screen surfaces and vice versa. The intervals might, for example, be one hour. [0167] Continue doing this for a sufficient time for a large fraction of the cells to have attached to the screens 1300. It is anticipated that this step might take about one to two days. [0168] After the cells are well seeded, rotate the screens (scaffold) 1300 to the vertical position or to the horizontal position as desired for dynamic culturing.

During dynamic culturing, leave the screens (scaffold) 1300 in either the vertical position or the horizontal position as desired. Place nutrients in the media, and slowly flow the media past the screens (scaffold) 1300 for the duration of dynamic culturing. The flow will be upward and generally parallel to or through (perpendicular to) the flat surfaces of the screens 1300 as desired.

After a sufficient time, harvest the cells.

In general, it is possible to execute any desired combination of positions of the rotor and scaffolds at particular stages of the seeding and cell culturing process. During dynamic culturing, the screens could be in either vertical or horizontal position during culturing, whichever is desired, and the flow could be either parallel to or through (perpendicular to) the screens.

Harvesting of Cells

In embodiments of the invention, there may be practiced certain techniques for harvesting cells from a scaffold 1300 after the cells have grown. It is known that tryp-LE E is useful for harvesting cells from a scaffold. In embodiments of the invention, for harvesting, of cells, the scaffolds will be washed with PBS three times and followed with addition of appropriate amount of tryp-LE E for about 30 minutes. Harvesting of cells may further be aided by the action of an impactor that impacts the cytoskeleton of the cells that is structurally connected to the screens (or scaffold). This impacting can dislodge cells through the mechanical force of the impact.

Computational Fluid Dynamics

Figure 19A:
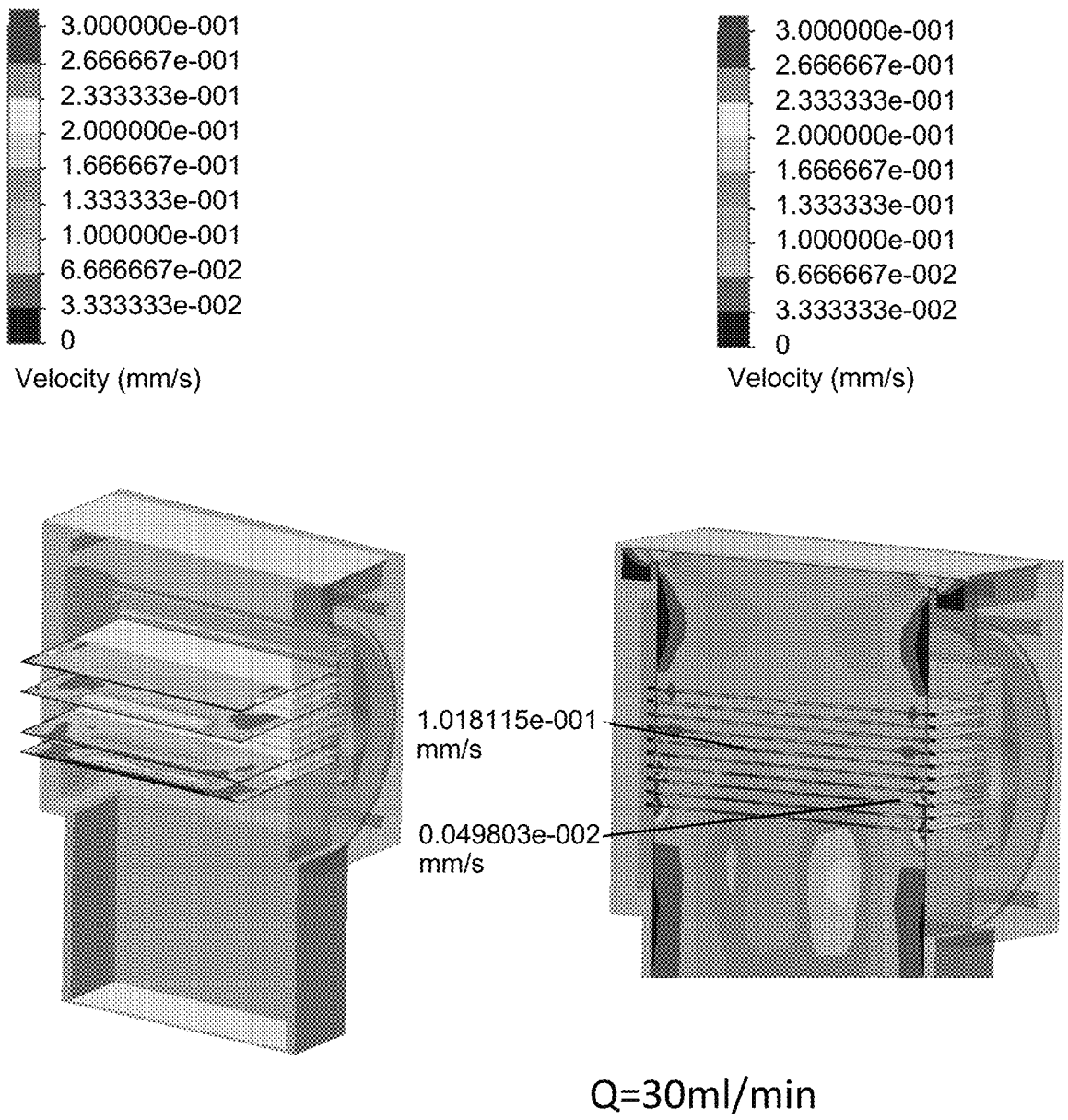
FIG. 19A shows results of Computational Fluid Dynamics modeling of the overall system at a first flowrate of liquid.
Figure 19B:
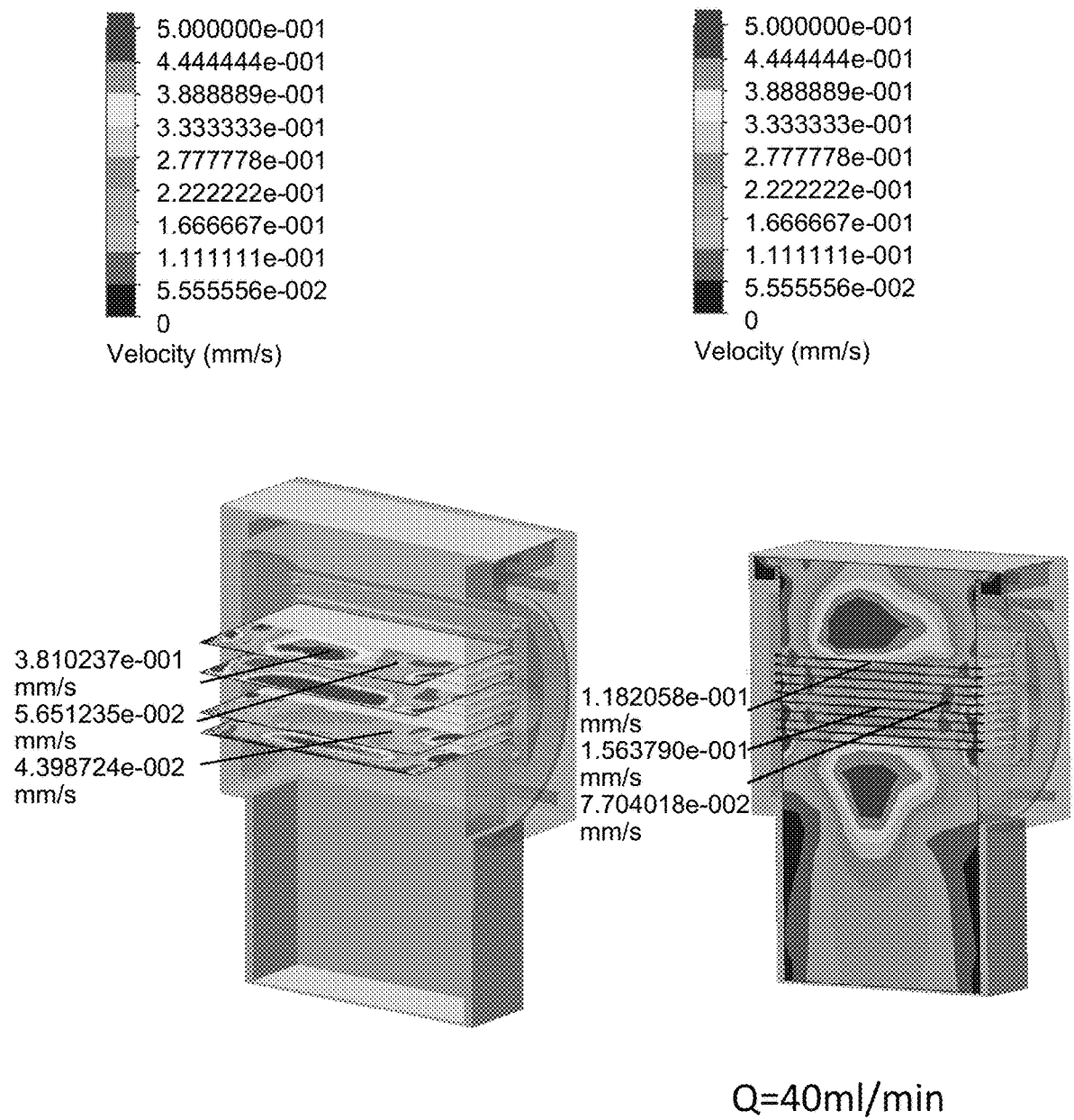
FIG. 19B shows results of Computational Fluid Dynamics modeling of the overall system at a second flowrate of liquid.
Figure 19C:
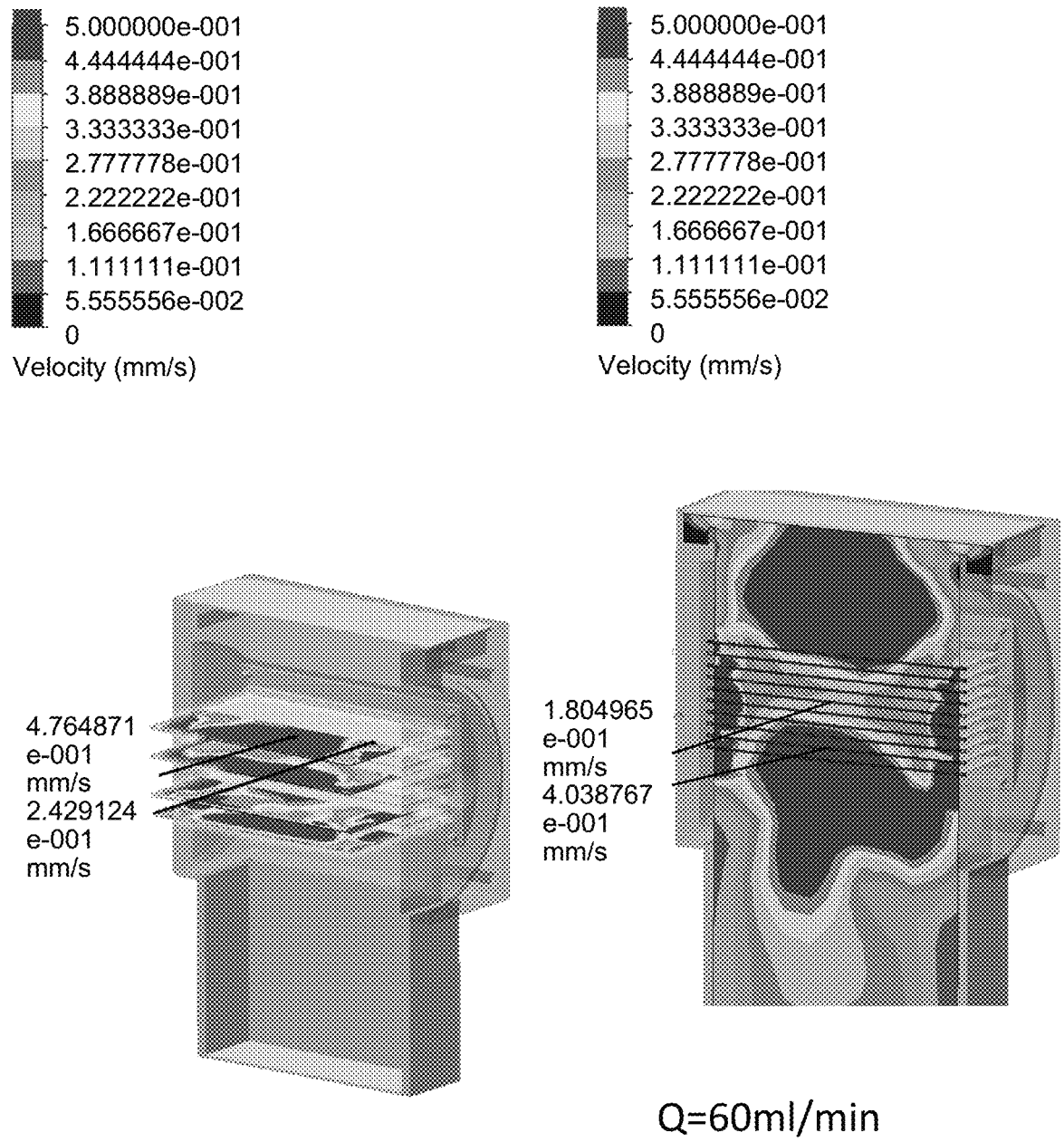
FIG. 19C shows results of Computational Fluid Dynamics modeling of the overall system at a third flowrate of liquid.
Figure 20:
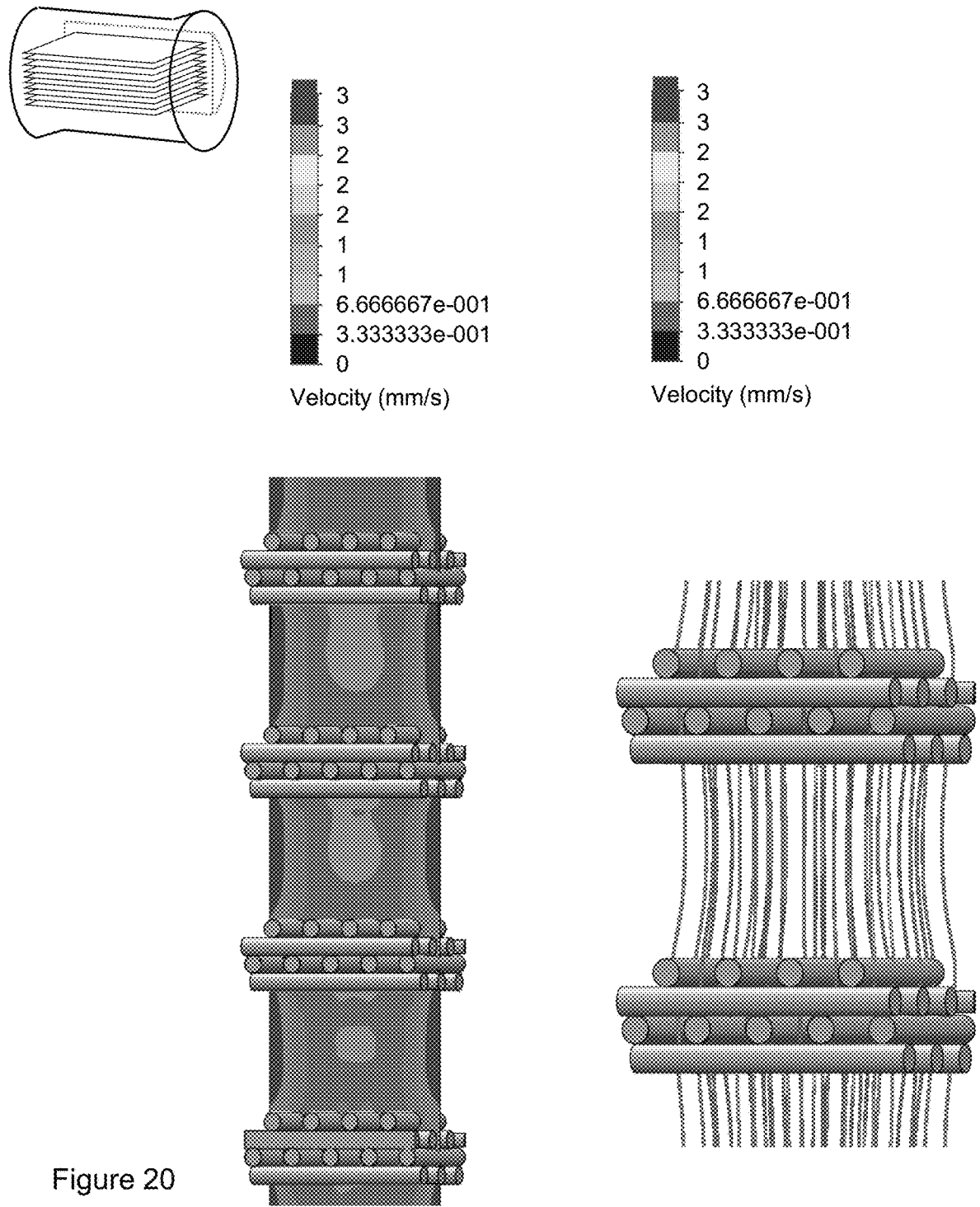
FIG. 20 shows results of Computational Fluid Dynamics modeling near individual screens. 10.

Referring now to FIGS. 19A-20, there are shown results of Computational Fluid Dynamics modeling of flow geometries of an embodiment of the invention. FIG. 19A shows local velocity distributions at a flowrate of 30 milliliters/minute (with a cross-sectional area in the incoming channel of approximately 6200 $mm^2$). FIG. 19B shows a velocity distribution for a flowrate of 40 milliliters/minute. FIG. 19C shows a velocity distribution for a flowrate of 60 milliliters/minute. FIG. 20 shows pressure distribution and streamlines of flow between screens that are constructed as described herein.

In general, any combination of disclosed features, components and methods described herein is possible. Steps of a method can be performed in any order that is physically possible.

All cited references are incorporated by reference herein.

Although embodiments have been disclosed, it is not desired to be limited thereby. Rather, the scope should be determined only by the appended claims.

What is claimed is:

1. A bioreactor, comprising:
a reservoir container for holding a liquid medium;
a duct providing a flowpath in a generally vertical direction upward from said reservoir container from a lower end of said duct to an upper end of said duct;
a plurality of fiber assemblies located within said duct, a top of said duct being at a higher elevation than a top of said plurality of fiber assemblies; and
a circulation system for causing said liquid medium to flow upwardly through said duct past or through said plurality of fiber assemblies;
wherein said upper end of said duct comprises an overflow wall surrounded on its outside by a moat, a bottom of said moat being at a lower elevation than said top of said overflow wall, said upper end of said duct and said moat being in contact with a pocket region, said pocket region being bounded by a structure that is connected to said duct, said pocket region being isolated from fluid communication with an exterior of said pocket region;
wherein when said circulation system is operating, said liquid medium flows over said overflow wall within said pocket region and said liquid medium is in contact with gas that is contained in said pocket region, and said liquid medium overflows into said moat and is removed from said moat by said circulation system.

2. The bioreactor of claim 1, further comprising a sump that is in fluid communication with said moat, said sump being at a lower elevation than said bottom of said moat, said circulation system being in fluid communication with said sump so as to withdraw liquid medium from said sump.

3. The bioreactor of claim 1, wherein a lower flow length exists from said lower end of said duct to a lower boundary of said plurality of fiber assemblies, and an upper flow length exists from said upper boundary of said plurality of fiber assemblies to said upper end of said duct, and wherein said upper flow length is shorter than said lower flow length.

4. The bioreactor of claim 1, wherein said duct has two pairs of parallel walls and said reservoir container has two pairs of parallel walls, and a pair of parallel walls of said duct is parallel to a pair of parallel walls of said reservoir container, and said duct is located midway between one of said pairs of parallel walls of said reservoir container.

5. The bioreactor of claim 1, further comprising an incubator enclosing said reservoir container and said duct, and further comprising a pump that removes gas from a gas space region of said reservoir container and ejects said gas outside said incubator.

6. The bioreactor of claim 1, wherein when said circulation system is operating, said liquid medium, after leaving said moat, flows through a pump and is returned to said reservoir container in a form of a shower that is dispensed from above a free liquid surface of said liquid medium in said reservoir container.

7. The bioreactor of claim 6, wherein when said circulation system is operating, said liquid medium in said shower is exposed to a gas contained in an above-liquid region within said reservoir container, said gas having a concentration of carbon dioxide that is larger than a carbon dioxide concentration in ambient air.

8. The bioreactor of claim 1, wherein said overflow wall occupies a plane that is generally parallel to one of said fiber structures.

9. The bioreactor of claim 1, wherein a gas space above said reservoir is a region that is fully enclosed except for having a first gas passageway through a boundary of said gas region, said first gas passageway containing therewithin a filter and being suitable for gas inflow, and a second gas passageway through said boundary of said gas region being suitable for gas outflow, said gas region having therethrough a showerhead capable of dispensing a shower of said liquid medium.

10. A bioreactor, comprising:
a reservoir container for holding a liquid medium;
a manifold assembly, said manifold assembly comprising an upper manifold and a lower manifold, said lower manifold having a lower end extending into said reservoir container;
a holder, said holder holding a plurality of fiber assemblies that are suitable as scaffolds for cells; said holder being able to be contained within said manifold assembly; and
a circulating system for causing said liquid medium to flow through said manifold assembly and through said holder,
wherein said manifold assembly and said holder provide a flowpath through said lower manifold and said holder and said upper manifold,
wherein said holder has grooves on an internal surface thereof, and has slots through an external surface thereof, and wherein said grooves and said slots are configured so that said fiber assemblies are able to be inserted through said slots and be supported by at least one of said grooves and said slots,
wherein said slots comprise rounded edges on an outward-facing surface or said grooves comprise rounded edges on an inward-facing surface that is opposite said slots.

11. The bioreactor of claim 10, wherein said rounded edges of said slots are hemicylindrical or said rounded edges of said grooves are hemicylindrical.

12. The bioreactor of claim 10, wherein said rounded edges of said slots adjoin a flat region that is generally parallel to one of said fiber assemblies or said rounded edges of said grooves adjoin a flat region that is generally parallel to one of said fiber assemblies.

13. The bioreactor system of claim 10, wherein said holder comprises two parts joinable to each other by engagement features and wherein said engagement features do not protrude interiorly beyond walls of said holder, and wherein one of said engagement features has therethrough a groove that is continuous with a groove in an adjacent portion of an interior surface of said holder.

14. The bioreactor of claim 10, wherein a groove-containing surface of said holder has openings therethrough to permit a pusher to position said fiber assemblies.

15. The bioreactor of claim 10, wherein said holder has a cross-sectional shape on either its inside or its outside or both that is rectangular with rounded corners.

16. A method of culturing cells, said method comprising the steps of:
providing a bioreactor, said bioreactor comprising:
a reservoir container for holding a liquid medium;
a manifold assembly, said manifold assembly comprising an upper manifold and a lower manifold, said lower manifold having a lower end extending into said reservoir container;
a holder, said holder being contained within said manifold assembly, said holder holding a plurality of fiber assemblies that are suitable for cells to grow on; and
a circulation system for causing the liquid medium to flow through said lower manifold and said fiber assemblies and said upper manifold;
seeding cells onto said fiber assemblies;
operating said circulation system under conditions appropriate for the cells to multiply into a plurality of cultured cells;
wherein said upper end of said duct comprises an overflow wall surrounded on its outside by a moat, a bottom of said moat being at a lower elevation than said top of said overflow wall, said upper end of said duct and said moat being in contact with a pocket region, said pocket region being bounded by a structure that is connected to said duct, said pocket region being isolated from fluid communication with an exterior of said pocket region;
wherein when said circulation system is operating, said liquid medium flows over said overflow wall within said pocket region and said liquid medium is in contact with gas that is contained in said pocket region, and said liquid medium overflows into said moat and is removed from said moat by said circulation system; and
harvesting the cultured cells from said bioreactor.

* * * * *